(12) United States Patent
Llop et al.

(10) Patent No.: US 12,343,223 B2
(45) Date of Patent: Jul. 1, 2025

(54) DENTAL BONE FOUNDATION GUIDE WITH PALATAL OR LINGUAL SIDE GAP AND FREEHAND SURGICAL GUIDE

(71) Applicant: NATONAL DENTEX, LLC, Jupiter, FL (US)

(72) Inventors: Daniel R. Llop, Cornelius, NC (US); Michael J. Mandeville, Reno, NV (US)

(73) Assignee: NATIONAL DENTEX, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/977,132

(22) Filed: Oct. 31, 2022

(65) Prior Publication Data

US 2023/0172688 A1 Jun. 8, 2023

Related U.S. Application Data

(63) Continuation of application No. 16/456,503, filed on Jun. 28, 2019, now Pat. No. 11,504,210.

(60) Provisional application No. 62/781,054, filed on Dec. 18, 2018, provisional application No. 62/697,549, filed on Jul. 13, 2018.

(51) Int. Cl.
*A61C 1/08* (2006.01)
*A61B 17/16* (2006.01)
*A61C 8/00* (2006.01)

(52) U.S. Cl.
CPC ............ *A61C 1/084* (2013.01); *A61C 8/0089* (2013.01); *A61B 17/1662* (2013.01)

(58) Field of Classification Search
CPC .............. A61B 2034/105; A61B 34/10; A61B 17/1662; A61B 17/16; A61B 17/176; A61C 1/084; A61C 1/085; A61C 8/0001; A61C 8/0089; A61C 8/0006; A61C 1/082; A61C 1/08
USPC ...................................................... 433/75, 76
See application file for complete search history.

(56) References Cited

U.S. PATENT DOCUMENTS

| | | | |
|---|---|---|---|
| 2013/0071811 A1* | 3/2013 | Groscurth | A61C 1/084 433/75 |
| 2017/0265963 A1* | 9/2017 | Yau | A61C 1/084 |
| 2019/0223988 A1* | 7/2019 | Palmer | A61C 8/001 |

* cited by examiner

*Primary Examiner* — Ralph A Lewis
*Assistant Examiner* — Mirayda A Aponte
(74) *Attorney, Agent, or Firm* — FROST BROWN TODD LLP

(57) ABSTRACT

A first guide member includes a horizontal body portion and a pair of upright portions. The horizontal body portion has an arcuate configuration and includes a first horizontal surface, a front surface, a rear surface, and a second horizontal surface. The first horizontal surface is flat. The first upright body portion includes a first inwardly extending portion. A first engagement surface of the first inwardly extending portion is configured to rest on a ridge of the alveolar arch of the patient. The second upright body portion includes a second inwardly extending portion. A second engagement surface of the second inwardly extending portion is configured to rest on a ridge of the alveolar arch of the patient. The first guide member lacks a component configured to extend along a lingual or palatal side of the alveolar arch of the patient.

20 Claims, 22 Drawing Sheets

DENTAL BONE FOUNDATION GUIDE WITH PALATAL OR LINGUAL SIDE GAP AND FREEHAND SURGICAL GUIDE

PRIORITY

This application is a continuation of U.S. patent application Ser. No. 16/456,503, entitled "Dental Bone Foundation Guide with Palatal or Lingual Side Gap and Freehand Surgical Guide," filed Jun. 28, 2019, issued as U.S. Pat. No. 11,504,210 on Nov. 22, 2022.

U.S. patent application Ser. No. 16/456,503 claims priority to U.S. Provisional Patent App. No. 62/697,549, entitled "Dental Bone Foundation Guide with Palatal or Lingual Side Gap," filed Jul. 13, 2018, the disclosure of which is incorporated by reference herein.

U.S. patent application Ser. No. 16/456,503 also claims priority to U.S. Provisional Patent App. No. 62/781,054, entitled "Dental Bone Foundation Guide with Palatal or Lingual Side Gap and Freehand Surgical Guide," filed Dec. 18, 2018, the disclosure of which is incorporated by reference herein.

BACKGROUND

Some patients may develop tooth loss warranting prosthetic replacement. Some instances may warrant a full dental arch restoration. To properly seat a permanent dental prosthetic, it may be necessary to remodel dental bone structures, thereby providing a substantially flat foundation for the prosthetic. After providing a substantially flat foundation, the dental surgeon may drill passageways into the bone in which to secure implants. Once these passageways are formed and the implants are secured therein, the surgeon may secure the prosthetic to the implants, thereby permanently affixing the prosthetic to the patient's bone.

Various forms of hardware may be used to perform the above-described surgical procedure. Examples of such hardware and associated procedures are described in U.S. Pat. No. 8,899,984, entitled "CT-Based, Side-Loading Surgical and Laboratory Dental Implant Guide System and Method," issued Dec. 2, 2014, the disclosure of which is incorporated by reference herein; U.S. Pat. No. 9,504,533, entitled "Endentulous Surgical Guide," issued Nov. 29, 2016, the disclosure of which is incorporated by reference herein; U.S. Pat. No. 9,693,834, entitled "Implant-Based Attachment System for Dental Implant Surgical Guide and Method," issued Jul. 4, 2017, the disclosure of which is incorporated by reference herein; U.S. Pat. No. 9,795,458, entitled "Dental Surgical Implant Guide and Prosthesis Combination and Method of Use," issued Oct. 24, 2017, the disclosure of which is incorporated by reference herein; U.S. Pub. No. 2014/0272778, entitled "Bone Foundation Guide and Method of Use," published Sep. 18, 2014, the disclosure of which is incorporated by reference herein; U.S. Pub. No. 2015/0010881, entitled "Bone Foundation Guide and Method of Use," published Jan. 8, 2015, the disclosure of which is incorporated by reference herein; U.S. Pub. No. 2016/0038255, entitled "Bone Foundation Guide System and Method," published Feb. 11, 2016, the disclosure of which is incorporated by reference herein; U.S. Pub. No. 2017/0112591, entitled "Bone Foundation Guide System and Method," published Apr. 27, 2017, the disclosure of which is incorporated by reference herein; U.S. Pub. No. 2017/0112592, entitled "Method of Using an Endentulous Surgical Guide," published Apr. 27, 2017, the disclosure of which is incorporated by reference herein; and U.S. Pub. No. 2017/0252126, entitled "Bone Foundation Guide System and Method," published Sep. 7, 2017, the disclosure of which is incorporated by reference herein.

While several dental surgical systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Exemplary Bone Foundation Guide

Figure 1:
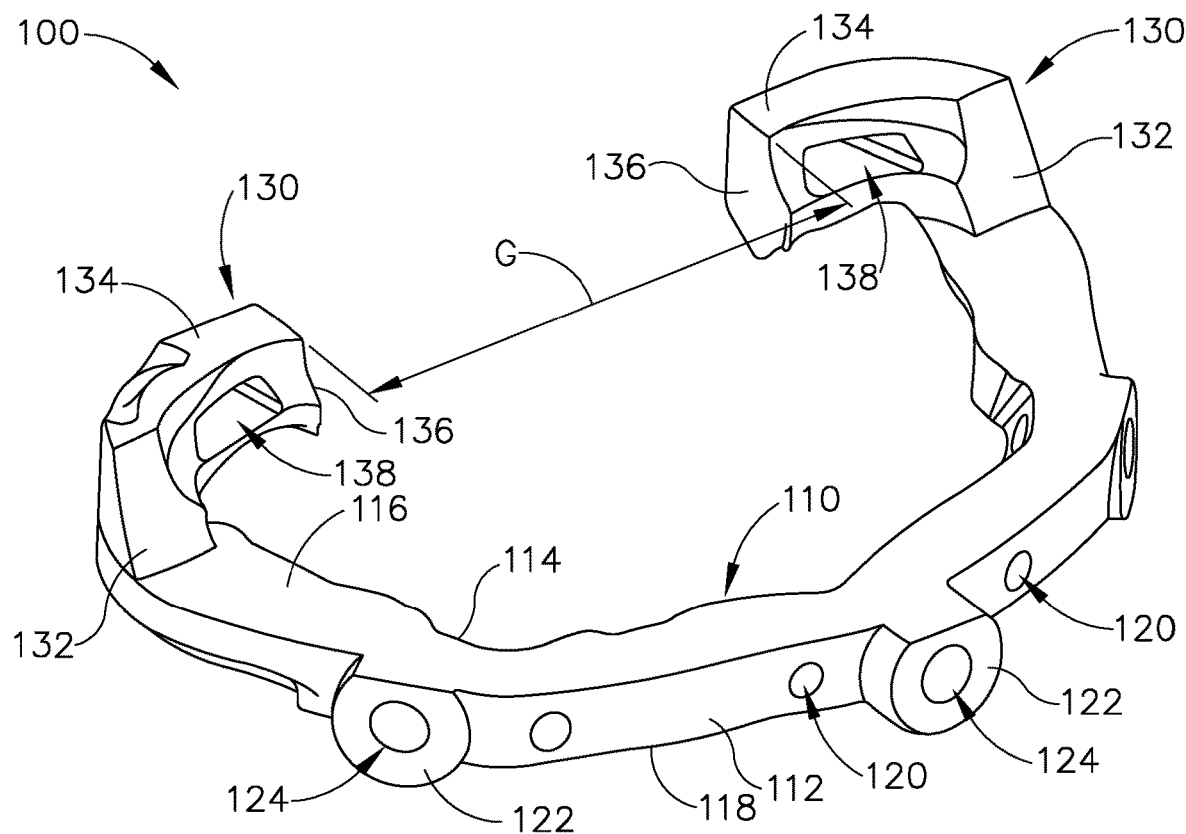
FIG. 1 depicts a perspective view of an exemplary bone foundation guide.
Figure 2:
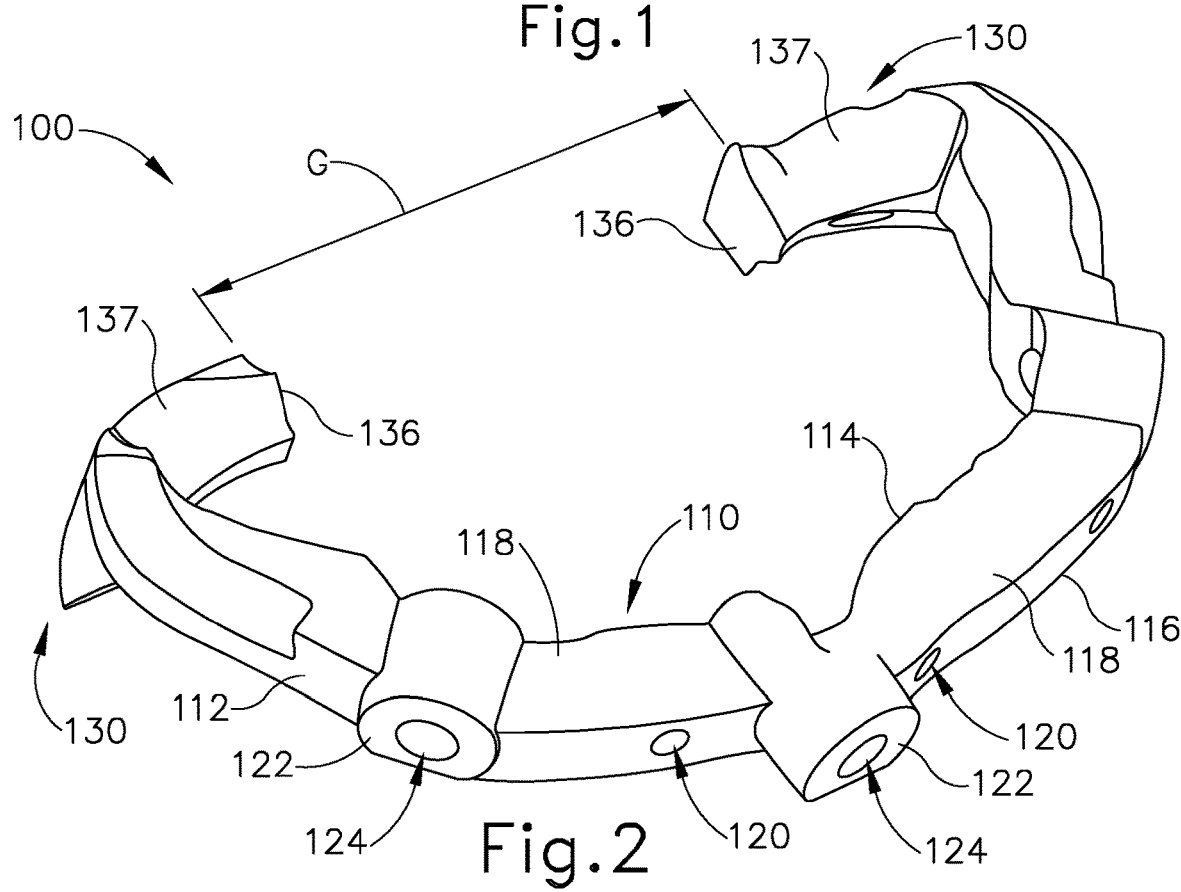
FIG. 2 depicts another perspective view of the bone foundation guide of FIG. 1.
Figure 3:
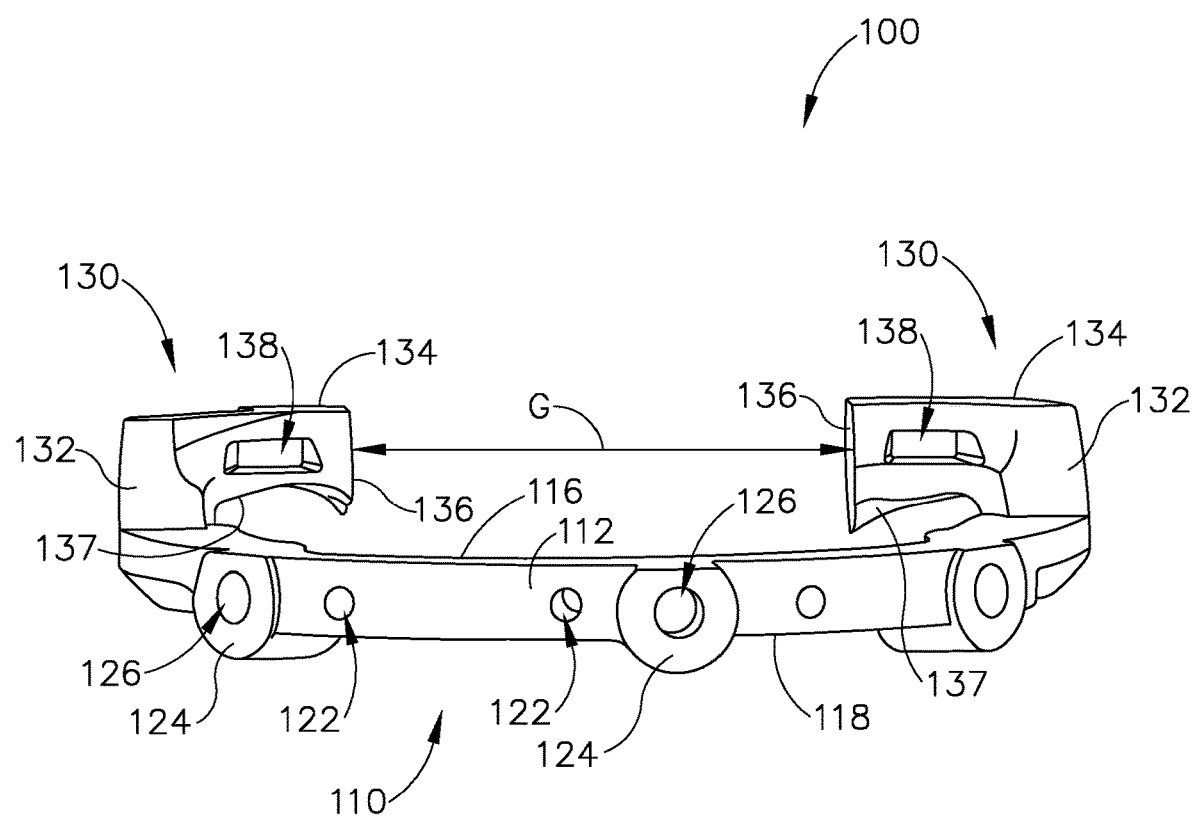
FIG. 3 depicts a front elevation view of the bone foundation guide of FIG. 1.
Figure 4:
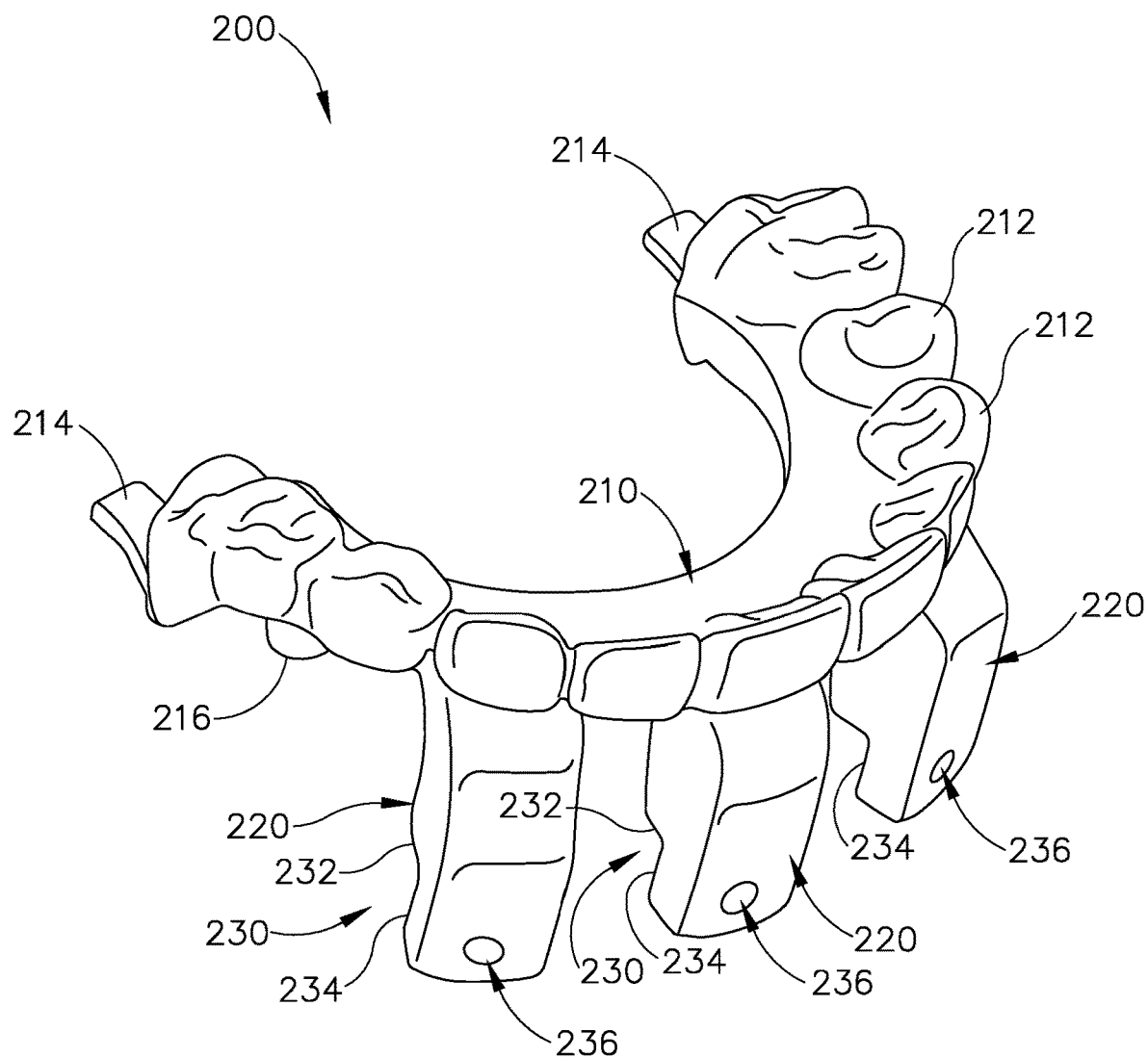
FIG. 4 depicts a perspective view of an exemplary strut assembly.

FIGS. 1-3 show an exemplary bone foundation guide (100), or bone reduction guide, that may be used in combination with other components in a surgical procedure as described below. Bone foundation guide (100) includes a horizontal body portion (110) and a pair of upright body portions (130). Horizontal body portion (110) extends along a horizontal plane and defines an arcuate shape corresponding to an alveolar arch of a patient, as described in greater detail below. Upright body portions (130) are located at each end of the arc defined by horizontal body portion (110). In some versions, bone foundation guide (100) is generated based on a three-dimensional digital model that is created based on a three-dimensional digital model of the patient's oral anatomy. Such a process may be performed in accordance with the teachings of any of the various patent references cited herein; and/or in accordance with the nSequence® Guided Prosthetics® Kit and workflow by National Dentex, LLC of Palm Beach Gardens, Florida.

Horizontal body portion (110) includes a front surface (112), a rear surface (114), an upper surface (116), and a lower surface (118). The terms "upper" and "lower" are being used herein in the exemplary context of bone foundation guide (100) and other devices being mounted to the mandibular alveolar arch. However, as noted below, some versions of bone foundation guide (100) may be mounted to the maxillary alveolar arch, in which cases upper surface (116) would in fact be presented downwardly; and lower source (118) upwardly. Use of the terms "upper" and "lower" should therefore not be read as limiting the alveolar ridge to which bone foundation guide (100) may be secured.

In the present example, rear surface (114) is configured to correspond directly to the configuration of the front-facing surface of the patient's alveolar arch, to thereby provide full surface-to-surface contact along the entirety of rear surface (114) when bone foundation guide (100) is fully seated on the alveolar arch. Rear surface (114) is thus configured to closely mate with a corresponding region of the bone structure of the alveolar arch of the patient. The configuration of rear surface (114) is customized per patient in this example, such that the configuration of rear surface (114) is based upon the anatomical surface geometry embodied in the three-dimensional digital model of the patient's anatomy. Upper surface (116) is substantially flat in this example, to thereby provide a substantially horizontal plane for guidance of a bone reduction procedure as described below.

Horizontal body portion (110) also includes a plurality of passageways (120, 124) extending from front surface (112) to rear surface (114). Passageways (120) are configured to align with corresponding passageways (236, 324) of a strut assembly (200) and a surgical guide (300) as will be described in greater detail below. Passageways (124) are configured to receive fasteners to secure bone foundation guide (100) to the alveolar ridge of a patient. By way of example only, bone foundation guide (100) may be secured to the alveolar ridge via pins, screws, or other features disposed in passageways (124). Passageways (124) are surrounded by cylindraceous stand-off features (122) in the present example. Stand-off features (122) are configured to reinforce the structural integrity of horizontal body portion (110) in the regions around passageways (124).

Each upright body portion (130) includes a vertically extending front surface (132), a horizontally extending upper surface (134), a vertically extending inner surface (136), and a lower surface (137). A slot (138) is formed through each upright body portion (130). In the present example, surfaces (132, 134, 136) are generally flat. A gap (G) extends laterally between inner surfaces (136). Lower surface (137) is configured to correspond directly to the configuration of an upwardly facing surface of the patient's alveolar arch (or the downwardly facing surface when bone foundation guide (100) is mounted to the maxillary alveolar arch), to thereby provide full surface-to-surface contact along the entirety of lower surface (137) when bone foundation guide (100) is fully seated on the alveolar arch. Lower surface (137) is thus configured to closely mate with the bone structure of a corresponding region of the alveolar ridge of the patient. The configuration of lower surface (137) is customized per patient in this example, such that the configuration of lower surface (137) is based upon the anatomical surface geometry embodied in the three-dimensional digital model of the patient's anatomy.

As best seen in FIG. 3, each lower surface (137) is positioned vertically higher than the horizontal plane of upper surface (116) in this example. Similarly, slots (138) are also positioned vertically higher than the horizontal plane of upper surface (116) in this example.

Those skilled in the art will recognize that bone foundation guide (100) of this example has only one single horizontal body portion (110) in this example. The single horizontal body portion (110) is configured to fit only on the buccal side of a patient's alveolar arch in this example—regardless of whether it is the mandibular alveolar arch or the maxillary alveolar arch—as will be described in greater detail below. Unlike conventional bone foundation guides, there is no additional horizontal body portion (110) that fits on the palatal or lingual side of the alveolar arch. This may provide in a reduced cost to manufacture bone foundation guide (100) due to the reduction of materials. Omitting a horizontal body portion (110) that fits on the palatal or lingual side of the alveolar arch may also reduce the amount of gum (G) tissue that needs to be moved away from bone (B) during installation of bone foundation guide (100) on the alveolar arch. The omission of a horizontal body portion (110) that fits on the palatal or lingual side of the alveolar arch may also improve the accuracy of seating of bone foundation guide (100) on the alveolar arch because the palatal or lingual tissue does not interfere with or otherwise contact horizontal body portion. In addition, the absence of a horizontal body portion (110) that fits on the palatal or lingual side of the alveolar arch may also improve visualization of anatomical structures such as arteries attached to gingiva, etc. The omission of a horizontal body portion (110) that fits on the palatal or lingual side of the alveolar arch may also assist in keeping the implant sites irrigated and cool. Other potential advantages of the configuration of bone foundation guide (100) of the present example will be apparent to those skilled in the art in view of the teachings herein.

By way of example only, bone foundation guide (100) may be formed using rapid prototyping equipment (e.g., 3D printing or other additive manufacturing, etc.), based on a three-dimensional digital model as noted above. By way of further example only, bone foundation guide (100) may be formed of plastic, metal, other materials, and combinations thereof. Various suitable ways in which bone foundation guide (100) may be formed will be apparent to those skilled in the art in view of the teachings herein.

II. Exemplary Strut Assembly

FIGS. 4-8 show an exemplary strut assembly (200) that may be used in combination with bone foundation guide (100) in a surgical procedure as described below. Strut assembly (200) includes a horizontal body portion (210) and a set of strut members (220). Horizontal body portion (210) extends along a horizontal plane and defines an arcuate shape corresponding to an alveolar arch of a patient, as described in greater detail below. A set of three-dimensional representations of prosthetic teeth (212) project upwardly from horizontal body portion (210). These teeth (212) correspond to the teeth of a full dental arch prosthetic device that will ultimately be installed on the patient's alveolar arch. Thus, the surface geometry of teeth (212) may be identical to the surface geometry of the teeth on the prosthetic device; with both being generated in a three-dimensional digital model using known techniques.

A pair of tabs (214) extend proximally from each free end of the arc formed by horizontal body portion (210). Tabs (214) provide structures for coupling strut assembly (200) with bone foundation guide (100) as described in greater detail below. The underside of body portion (210) includes a set of downwardly projecting studs (216). Studs (216) of the present example serve as anatomical bone positioning stops and are configured to engage anatomical structures of the alveolar ridge when the combination of strut assembly (200) and bone foundation guide (100) are mounted to the alveolar ridge, as described in greater detail below. In some variations, studs (216) are omitted.

Figure 5:
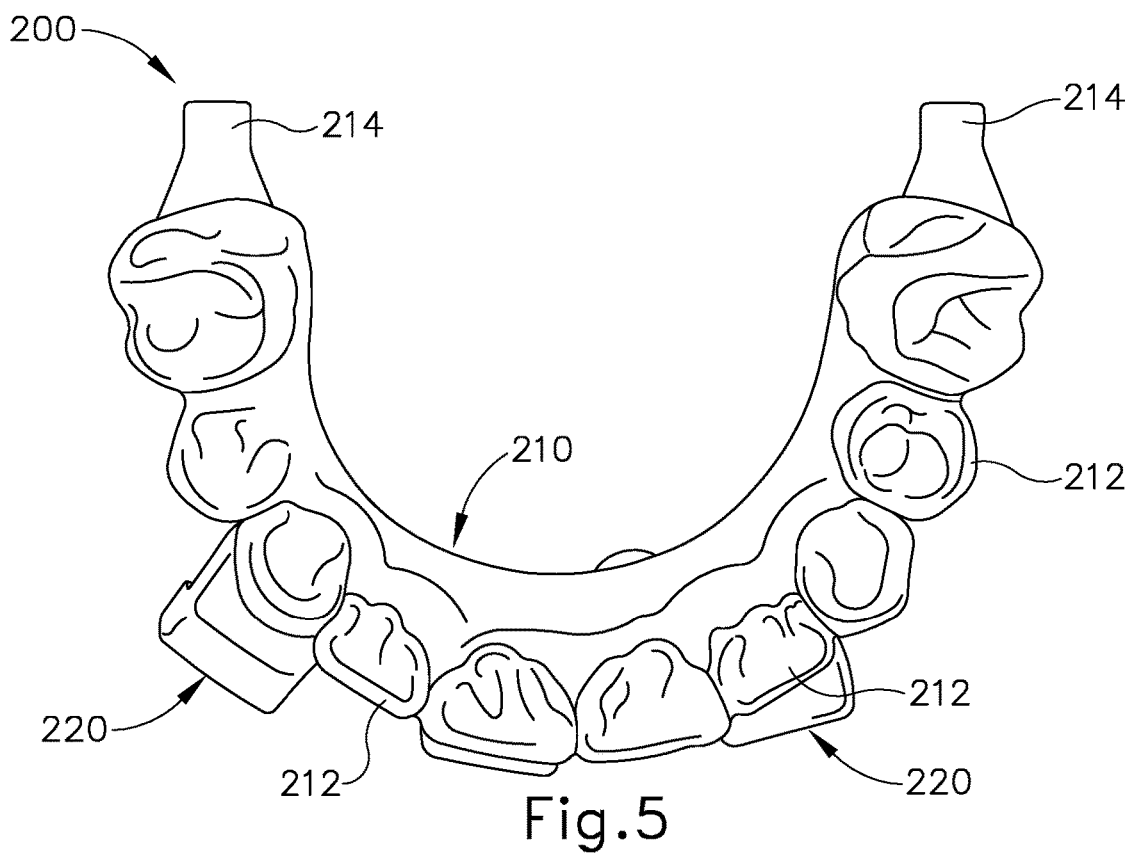
FIG. 5 depicts a top plan view of the strut assembly of FIG. 4.
Figure 6:
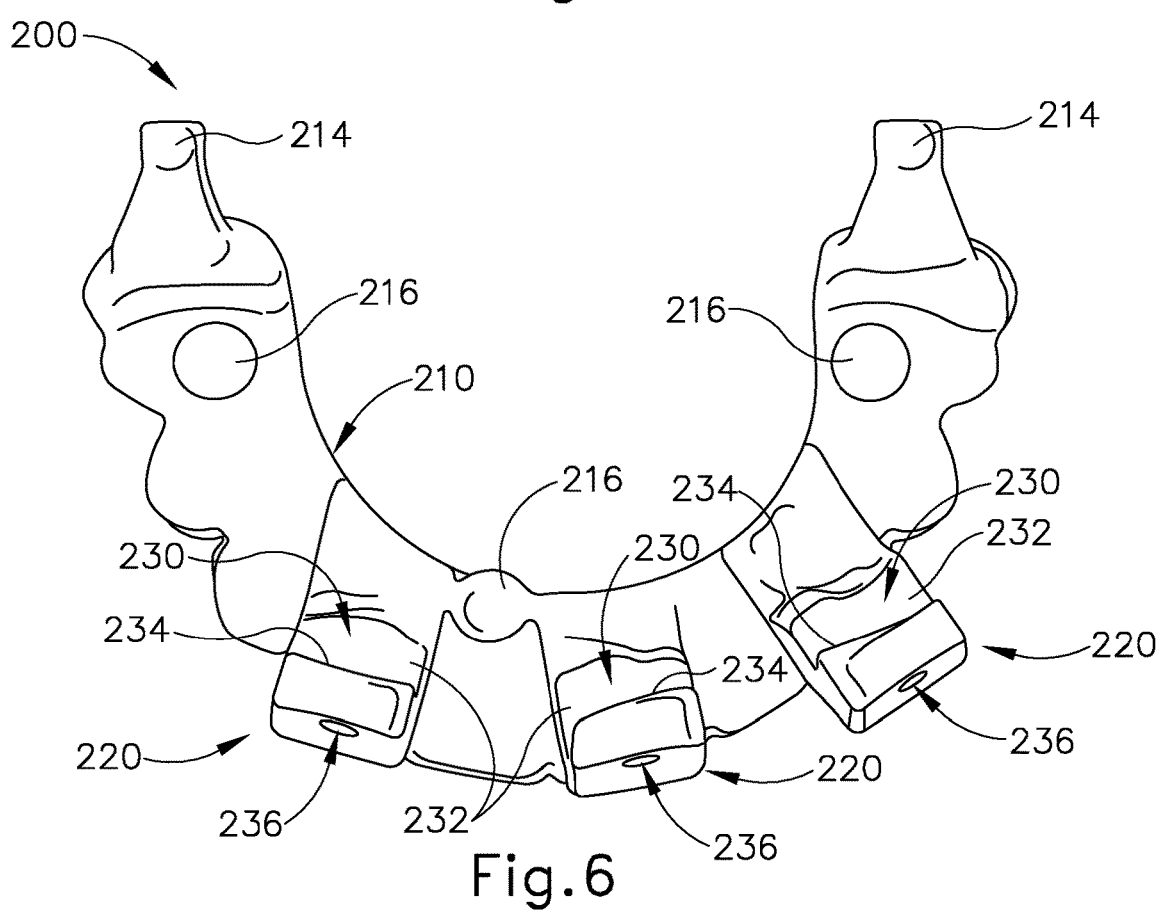
FIG. 6 depicts a bottom plan view of the strut assembly of FIG. 4.
Figure 7:
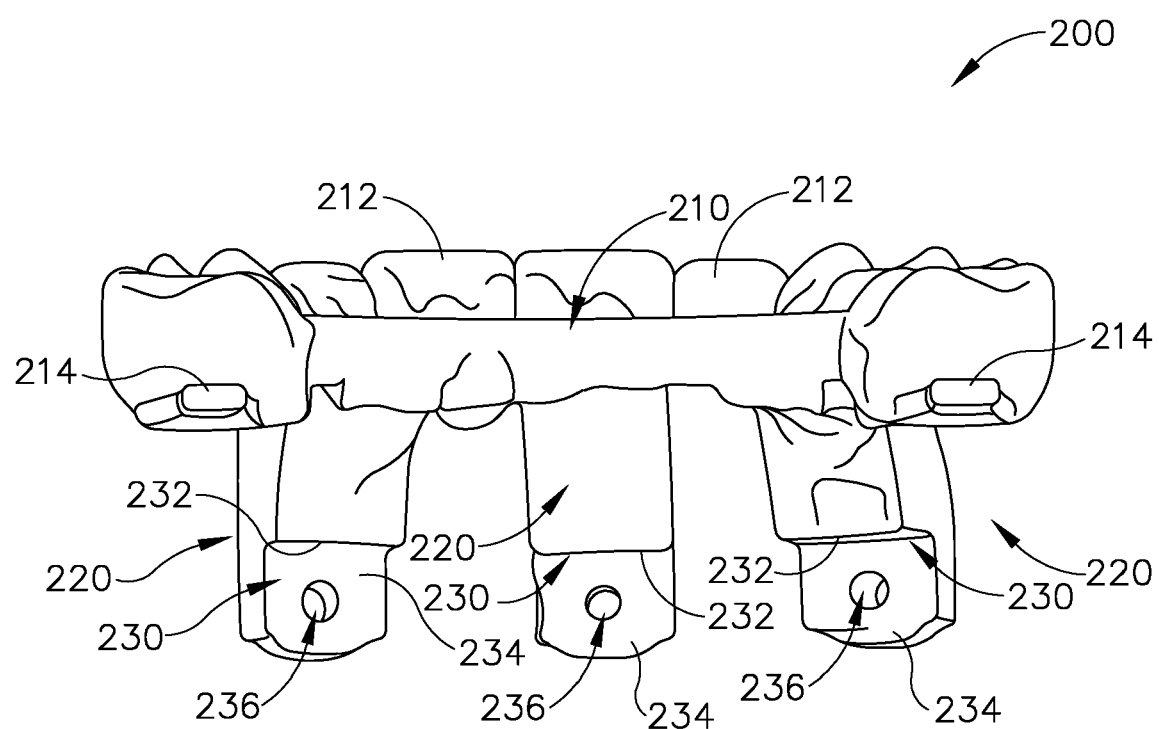
FIG. 7 depicts a rear elevation view of the strut assembly of FIG. 4.
Figure 8:
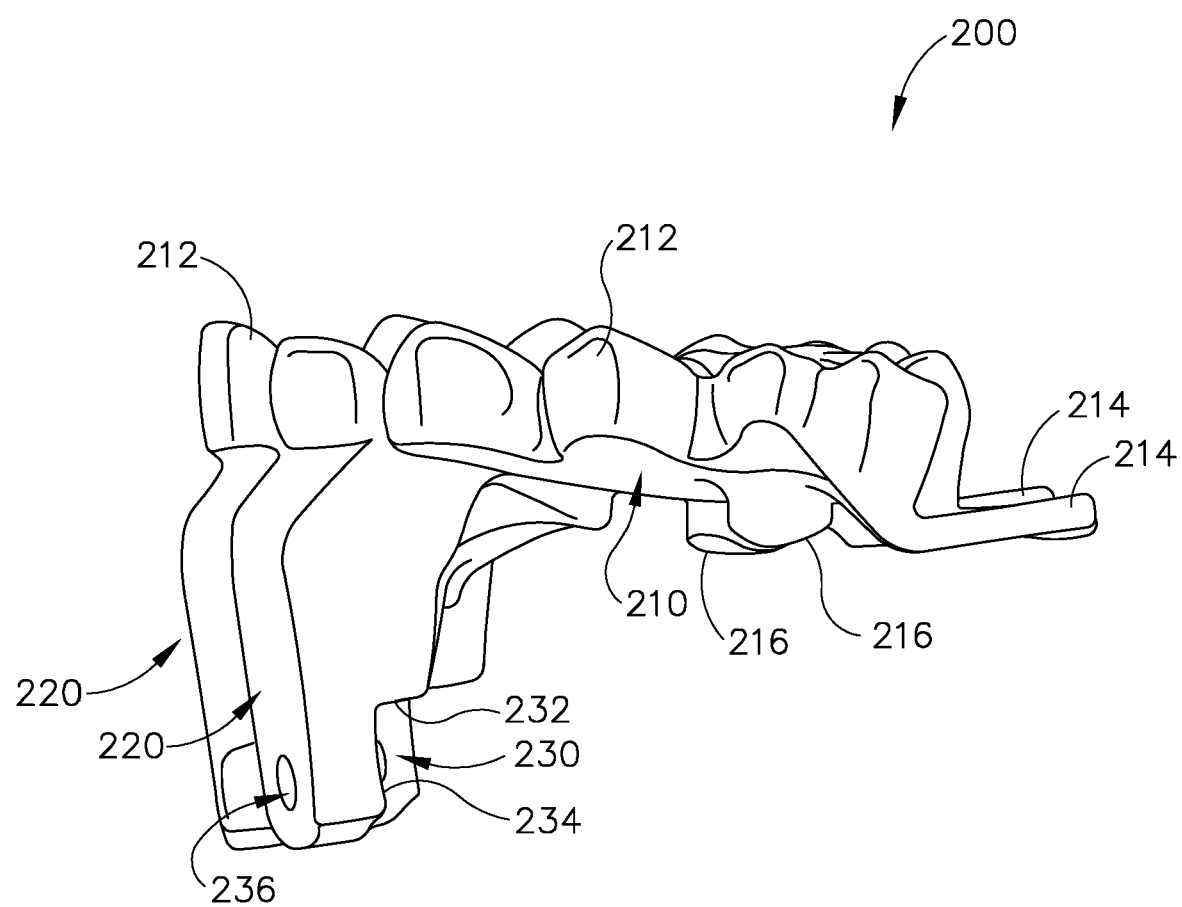
FIG. 8 depicts a side elevation view of the strut assembly of FIG. 4.

Strut assembly (200) includes three strut members (220) in the present example, though strut assembly (200) may instead include more or fewer than three strut members (220). Each strut member (220) includes a passageway (236) and a shelf portion (230). Each shelf portion (230) includes a downwardly facing surface (232) and a rear facing surface (234). Surfaces (232, 234) together form a right angle in this example. As best seen in FIG. 5, portions of one or more strut members (220) may project distally past the arc of teeth (212).

By way of example only, strut assembly (200) may be formed using rapid prototyping equipment (e.g., 3D printing or other additive manufacturing, etc.), based on a three-dimensional digital model as noted above. By way of further example only, strut assembly (200) may be formed of plastic, metal, other materials, and combinations thereof. Various suitable ways in which strut assembly (200) may be formed will be apparent to those skilled in the art in view of the teachings herein.

Figure 9:
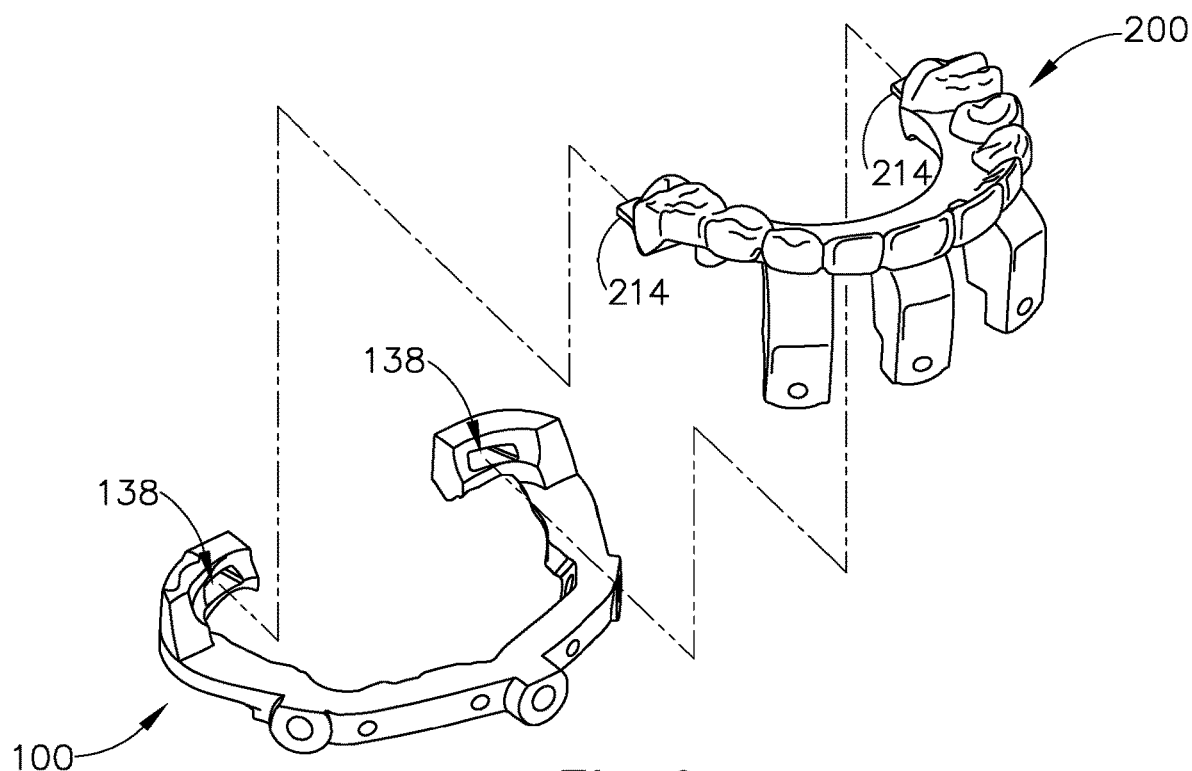
FIG. 9 depicts an exploded perspective view of a combination of the bone foundation guide of FIG. 1 and the strut assembly of FIG. 4.
Figure 10:
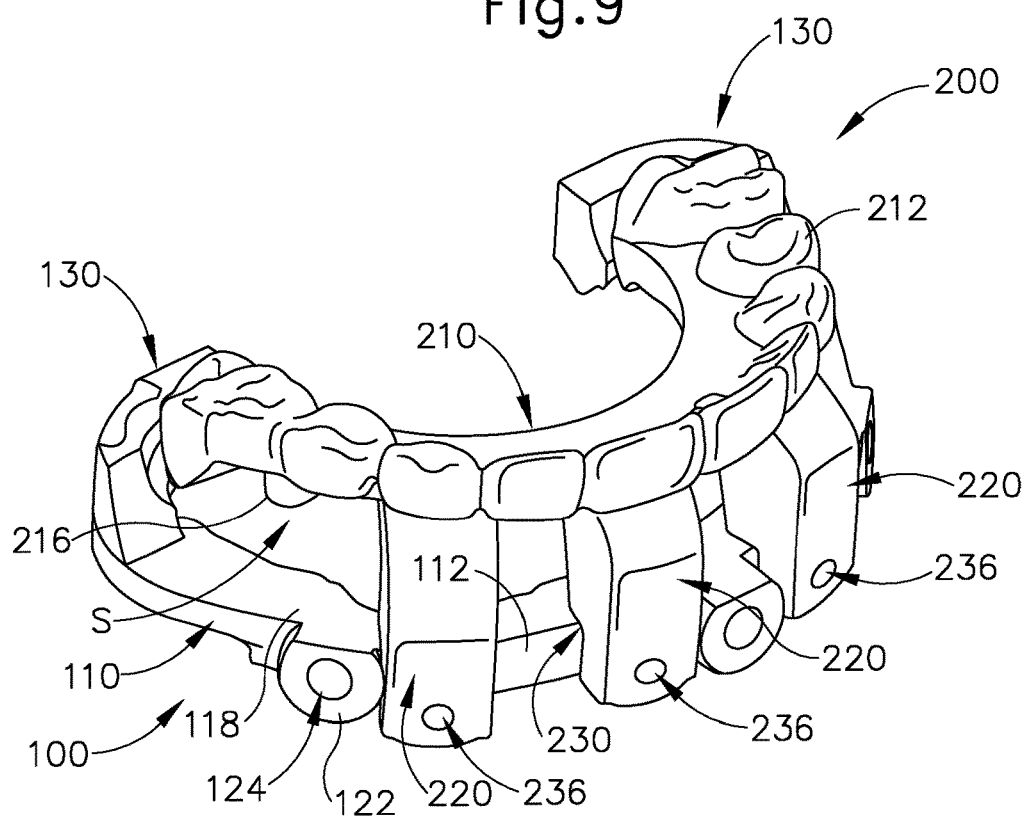
FIG. 10 depicts a perspective view of the strut assembly of FIG. 4 assembled with the bone foundation guide of FIG. 1.
Figure 11:
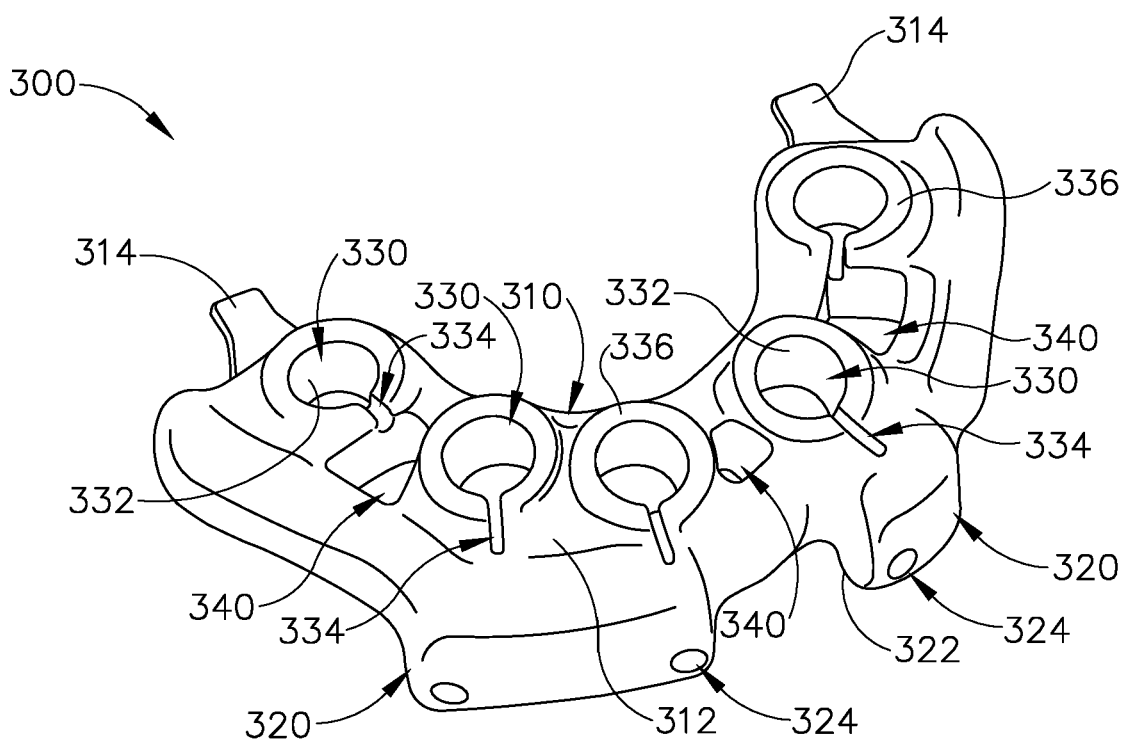
FIG. 11 depicts a perspective view of an exemplary surgical guide.
Figure 12:
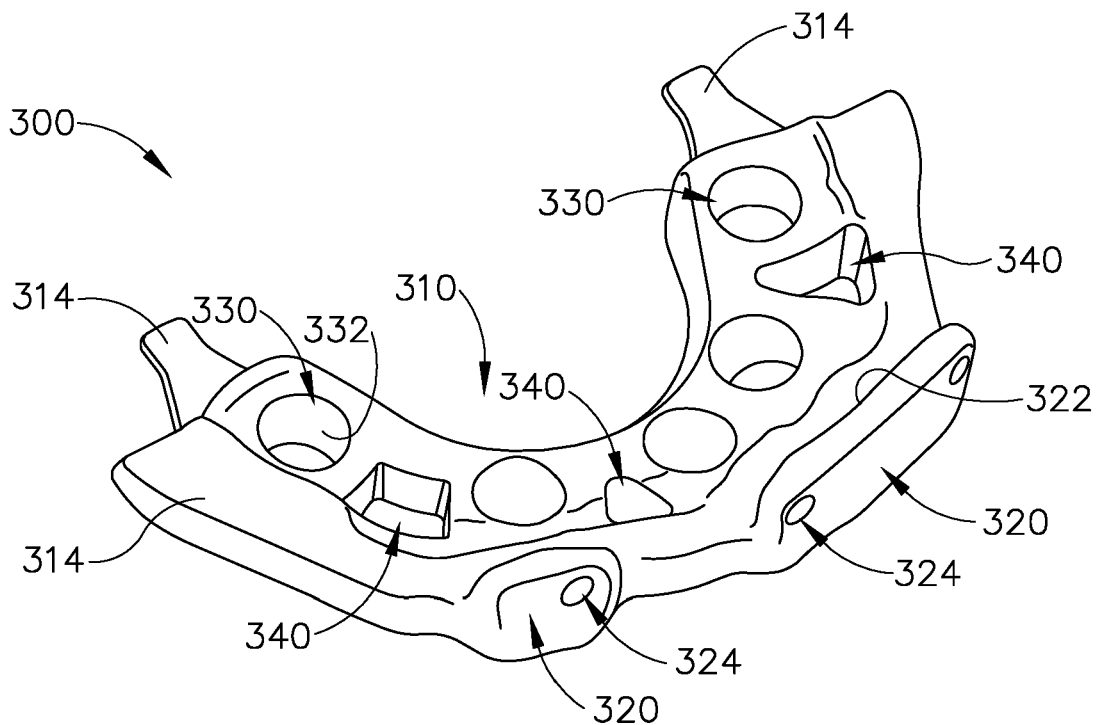
FIG. 12 depicts another perspective view of the surgical guide of FIG. 11.
Figure 13:
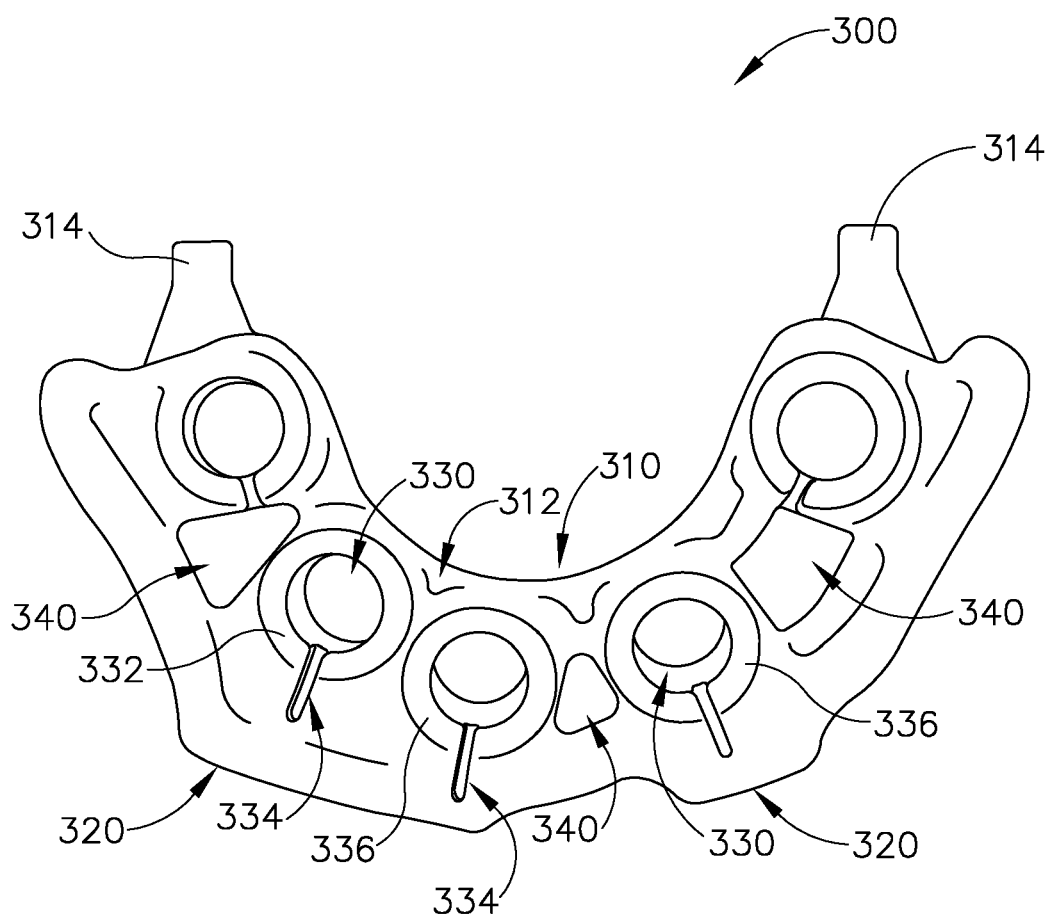
FIG. 13 depicts a top plan view of the surgical guide of FIG. 11.
Figure 14:
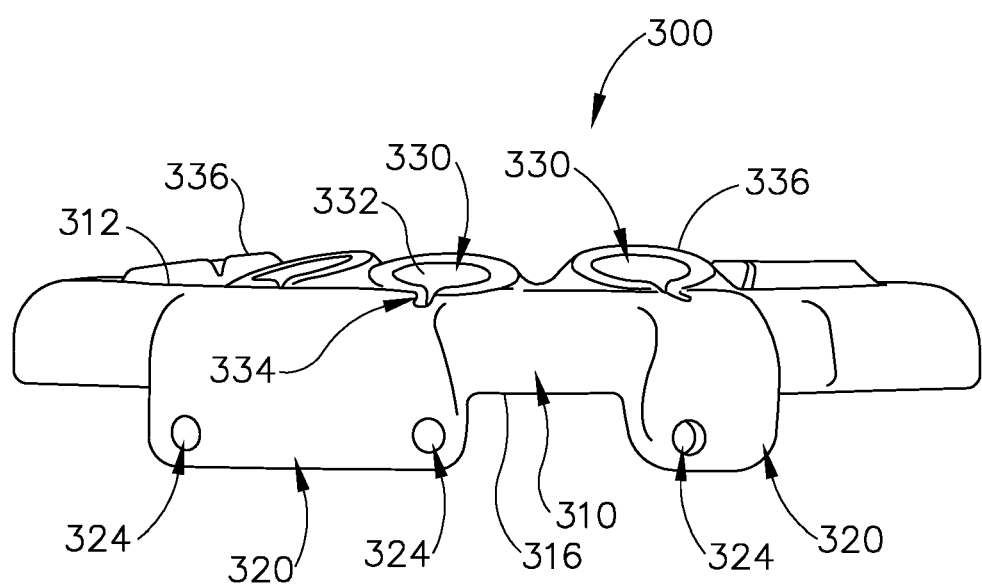
FIG. 14 depicts a front elevation view of the surgical guide of FIG. 11.
Figure 15:
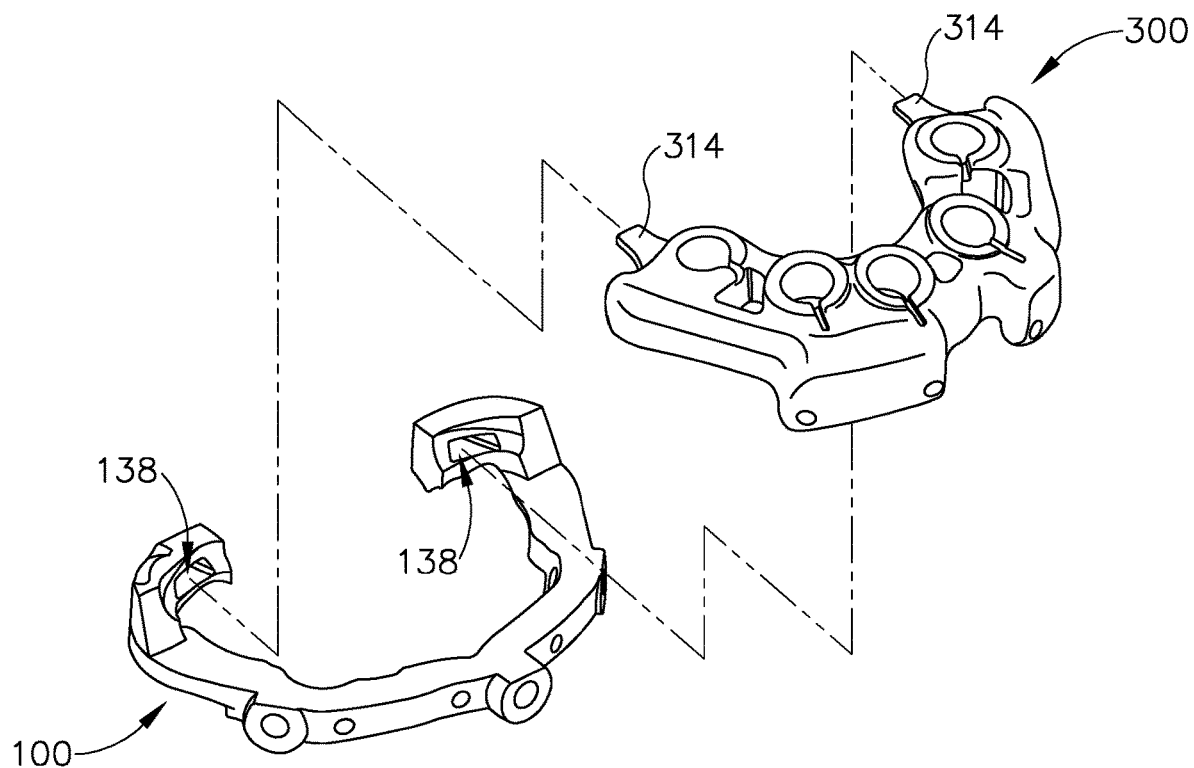
FIG. 15 depicts an exploded perspective view of a combination of the bone foundation guide of FIG. 1 and the surgical guide of FIG. 11.
Figure 16:
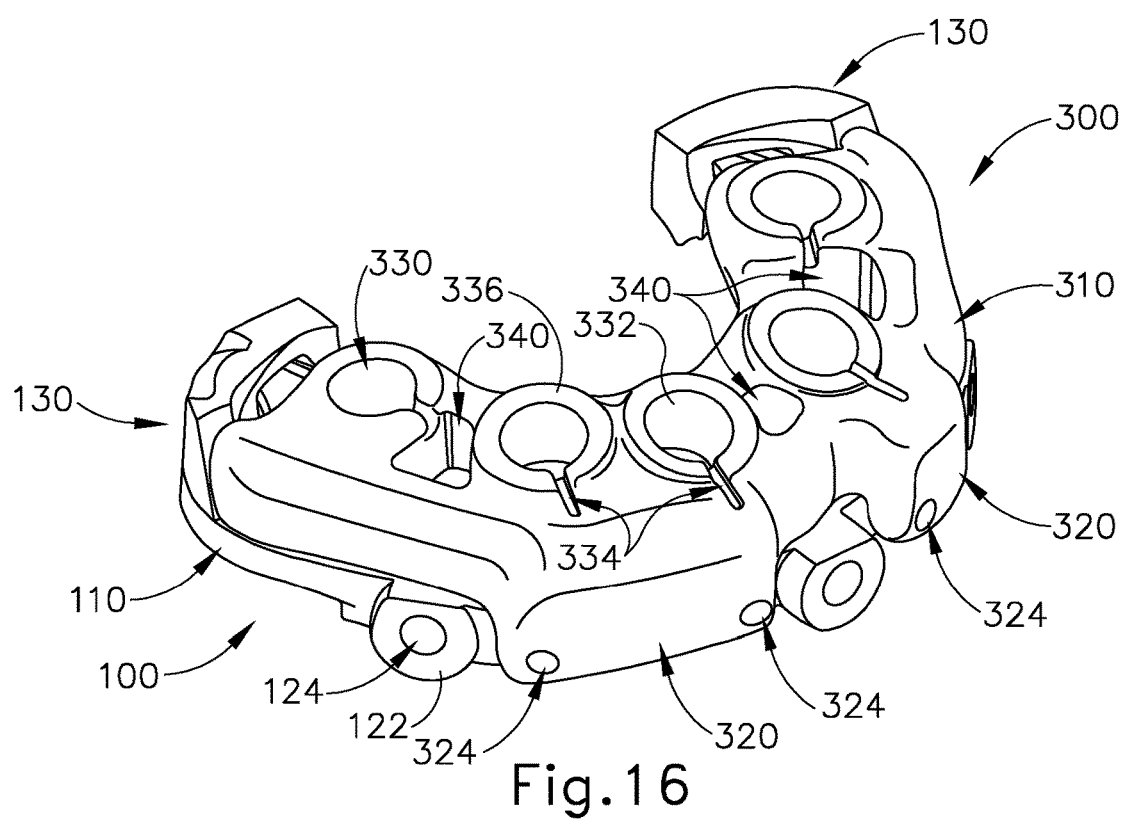
FIG. 16 depicts a perspective view of the surgical guide of FIG. 11 assembled with the bone foundation guide of FIG. 1.
Figure 17:
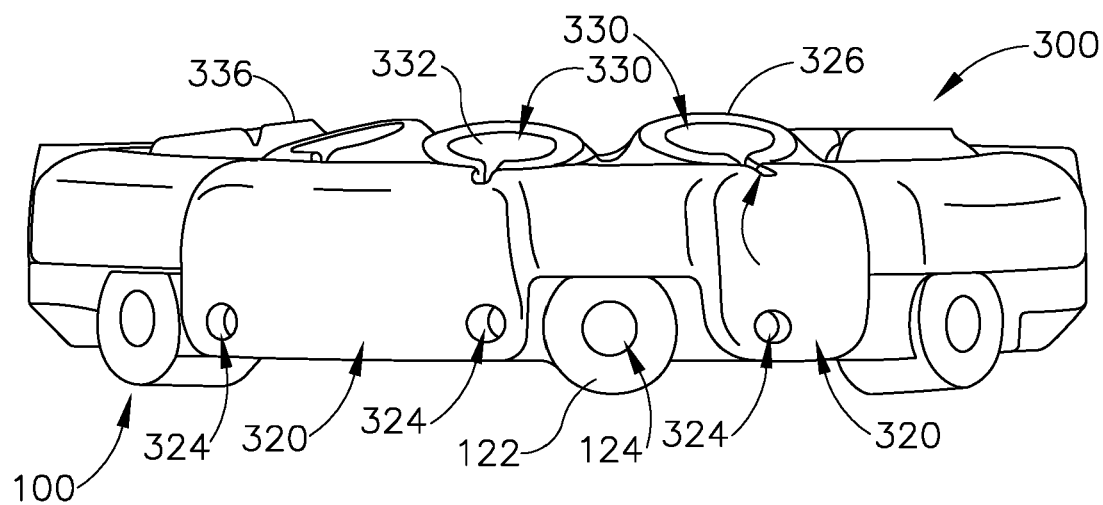
FIG. 17 depicts a front elevation view of the surgical guide of FIG. 11 assembled with the bone foundation guide of FIG. 1.
Figure 18:
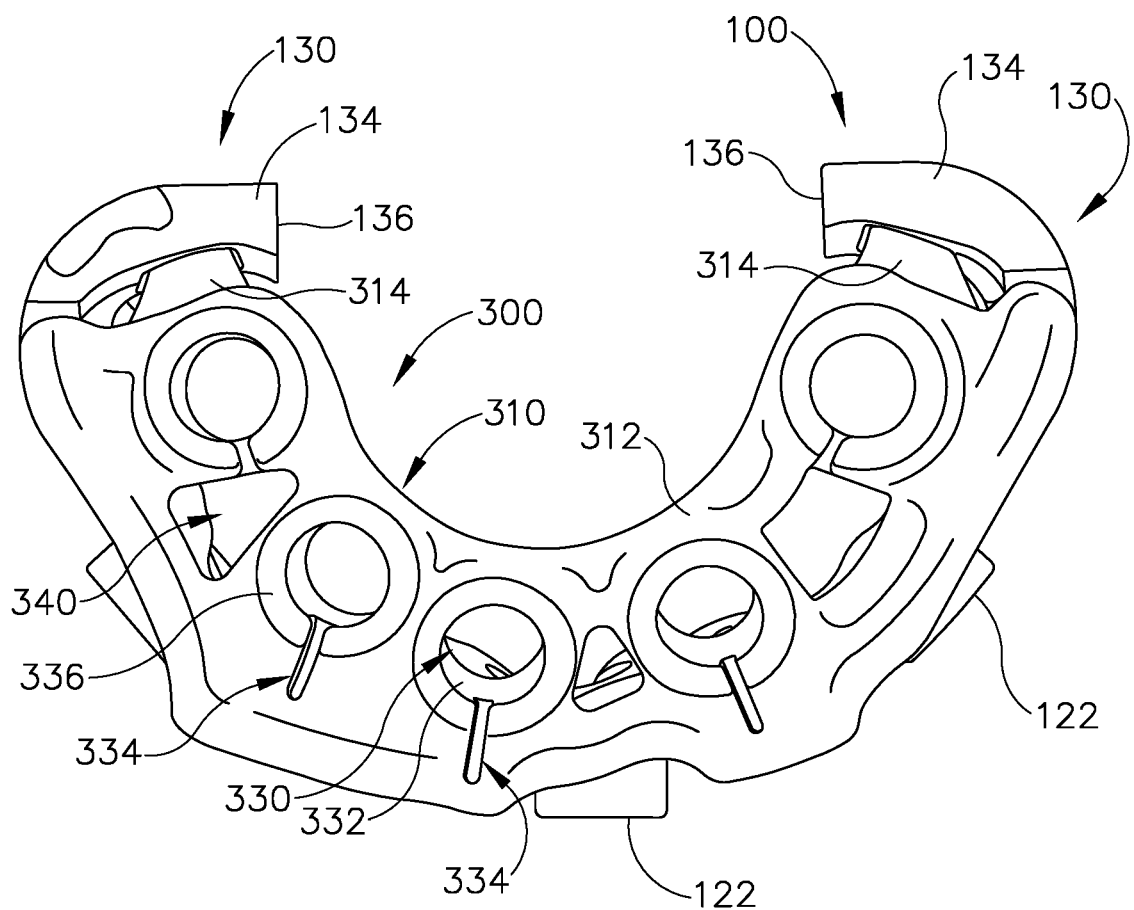
FIG. 18 depicts a top plan view the surgical guide of FIG. 11 assembled with the bone foundation guide of FIG. 1.

FIGS. 9-10 show how strut assembly (200) and bone foundation guide (100) may be coupled together. As shown, tabs (214) of strut assembly (200) may be inserted into corresponding slots (138) of bone foundation guide (100). Strut members (220) of strut assembly (200) are configured to engage horizontal body portion (110) of bone foundation guide (100). When strut members (220) are engaged with horizontal body portion (110), shelf portions (230) of strut members (220) receive horizontal body portion (110). Thus, each downwardly facing surface (232) of each strut member (220) engages upper surface (118) of horizontal body portion (110); and each rear facing surface (232) of each strut member (220) engages front surface (112) of horizontal body portion (110). Passageways (236) of strut members (220) are aligned with passageways (122) of horizontal body portion (110) when strut assembly (200) is coupled with bone foundation guide (110). The height of strut members (220) puts teeth (210) in position for normal occlusal engagement with the teeth of the other alveolar ridge of the patient, as will be described in greater detail below.

III. Exemplary Surgical Guide

FIGS. 11-14 show an exemplary surgical guide (300) that may be used in combination with bone foundation guide (100) in a surgical procedure as described below. Surgical guide (300) includes a horizontal body portion (310) and a set of flange members (320). Horizontal body portion (310) extends along a horizontal plane and defines an arcuate shape corresponding to an alveolar arch of a patient, as described in greater detail below. A set of guide passageways (330) extend through horizontal body portion (310). Each guide passageway (330) includes a cylindraceous inner surface (332), a flat top surface (336), and a guide notch (334).

Inner surfaces (332) are oriented to guide a conventional drilling instrument along the appropriate path to drill openings to receive implants as will be described in greater detail below. Inner surfaces (332) may also assist in guiding instrumentation used to install the implants in the openings after the openings are drilled in the alveolar arch. Moreover, inner surfaces (332) may assist in guiding instrumentation used to install abutments on the implants after the implants are installed in the alveolar arch. In some instances, one or more inner surfaces (332) may be vertically oriented, such that inner surfaces (332) are perpendicular to the horizontal plane associated with horizontal body portion (310). In other instances, one or more inner surfaces (332) may be obliquely oriented relative to the horizontal plane associated with horizontal body portion (310). In the present example, each top surface (336) is perpendicular to the adjacent inner surface (332), regardless of whether inner surface (332) is perpendicular or oblique relative to the horizontal plane associated with horizontal body portion (310). Top surfaces (336) are configured to provide a hard stop for master tube insertion into the corresponding guide passageways (330), thereby controlling the depth of implants that are inserted into bone (B) via passageways (330). In other words, top surfaces (336) may engage corresponding implant mount flanges to thereby arrest insertion of implants via passageways (330) at corresponding predetermined depths of insertion.

Each guide notch (334) is positioned at a prescribed angular orientation about the longitudinal axis of the corresponding guide passageway (330). The angular orientations of guide notches (334) may vary from patient to patient; and the angular orientations of guide notches (334) may vary from guide passageway (330) to guide passageway (330) within the same surgical guide (300). Each guide notch (334) is configured and oriented to provide the surgeon with a visual cue as to where to angularly align a corresponding notch of an implant mount that is inserted via the corresponding guide passageway (330). This may ensure accurate rotation of the dental implant and corresponding dental implant abutment to line up properly with the predetermined exit hole in the top of a dental prosthesis that will ultimately be secured to the dental implant abutments.

A pair of tabs (314) extend proximally from each free end of the arc formed by horizontal body portion (310). Tabs (314) provide structures for coupling surgical guide (300) with bone foundation guide (100) as described in greater detail below. Horizontal body portion (310) also includes a set of openings (340) extending vertically through horizontal body portion (310), from a top surface (312) of horizontal body portion (310) to a bottom surface (316) of horizontal body portion (310). Openings (340) may assist in providing windows for visualization of bone (B) underneath surgical guide (300), as well as visualization of dental drills and implants inserted through guide passageways (330). Openings (340) may also provide additional pathways for irrigation fluid (e.g., water, saline, etc.) to reach bone (B) underneath surgical guide (300).

Surgical guide (300) includes two flange members (320) in this example, though surgical guide (300) may instead include more or fewer than two flange members (320). One flange member (320) includes two passageways (324) while the other flange member (320) includes only one passageway (324) in this example. Each flange member (320) includes a rear facing surface (322). Flange members (320) are positioned along the distal or buccal side of body portion (310) and are thereby positioned to engage front surface (112) of bone foundation guide (100) as will be described in greater detail below.

By way of example only, surgical guide (300) may be formed using rapid prototyping equipment (e.g., 3D printing or other additive manufacturing, etc.), based on a three-dimensional digital model as noted above. By way of further example only, surgical guide (300) may be formed of plastic, metal, other materials, and combinations thereof. In some versions, the majority of surgical guide (300) is formed of plastic, while guide passageways (330) are lined with metallic cylinders. Various suitable ways in which surgical guide (300) may be formed will be apparent to those skilled in the art in view of the teachings herein.

FIGS. 15-18 show how surgical guide (300) and bone foundation guide (100) may be coupled together. As shown, tabs (314) of surgical guide (300) may be inserted into corresponding slots (138) of bone foundation guide (100). Bottom surface (316) of horizontal body portion (310) of surgical guide (300) rests atop upper surface (116) of horizontal body portion (110) of bone foundation guide (100). Each rear facing surface (322) of each flange member (320) engages front surface (112) of horizontal body portion (110). Passageways (324) of flange members (320) are aligned with passageways (122) of horizontal body portion (110) when surgical guide (300) is coupled with bone foundation guide (110). When surgical guide (300) and bone foundation guide (100) are coupled together, passageways (330) are positioned and aligned to structurally guide the drilling of openings for implants and the installation of implants in the drilled openings, as will be described in greater detail below.

IV. Exemplary Surgical Procedure

Figure 19:
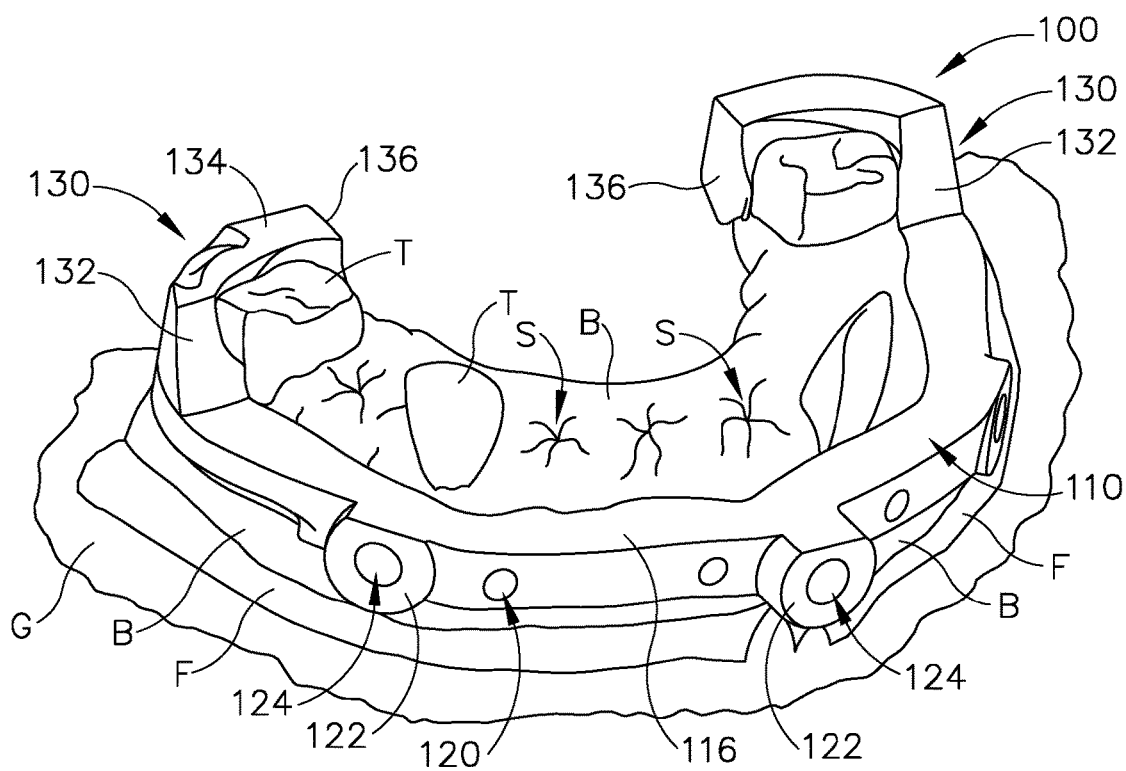
FIG. 19 depicts a perspective view of the bone foundation guide of FIG. 1 mounted to an alveolar ridge of a patient, before a bone reduction procedure.

FIGS. 19-22 show different stages of an exemplary surgical procedure in which bone foundation guide (100), strut assembly (200), and surgical guide (300) are used. As shown in FIG. 19, bone foundation guide (100) is positioned over an alveolar arch of a patient. In the present example, the alveolar arch is the mandibular alveolar arch, though the same procedure and similar equipment may be used on the maxillary alveolar arch. The only difference would be the bone foundation guide (100), strut assembly (200), and surgical guide (300) having customized configurations to fit on the maxillary alveolar arch.

As shown, before bone foundation guide (100) is installed, the surgeon incises the gum (G) along the ridge of the alveolar arch and peels the gum (G) away, leaving flaps (F) to reveal bone (B). In the present example, bone foundation guide (100) rests entirely on bone (B), without being supported by any gum (G) tissue. As is also shown in FIG. 19, the patient in this case is missing several teeth, leaving behind sockets (S), with a few teeth (T) remaining. In order to fixedly secure bone foundation guide (100) to the bone (B), the surgeon may drive pins, screws, or other fastener devices through passageways (124). Such fastener devices may be removable to facilitate removal of bone foundation guide (100) after the procedure is complete. With bone foundation guide (100) being installed on the bone (B), horizontal body portion (110) extends only along the buccal side of the alveolar arch. No horizontally extending portion of bone foundation guide (100) wraps along the lingual (or palatal) side of the alveolar arch. Lower surfaces (137) of upright body portions (130) rest on the upper ridge of the alveolar arch, thereby supplementing the structural support provided by the fastener devices that are disposed in passageways (124) and bone (B).

Figure 20:
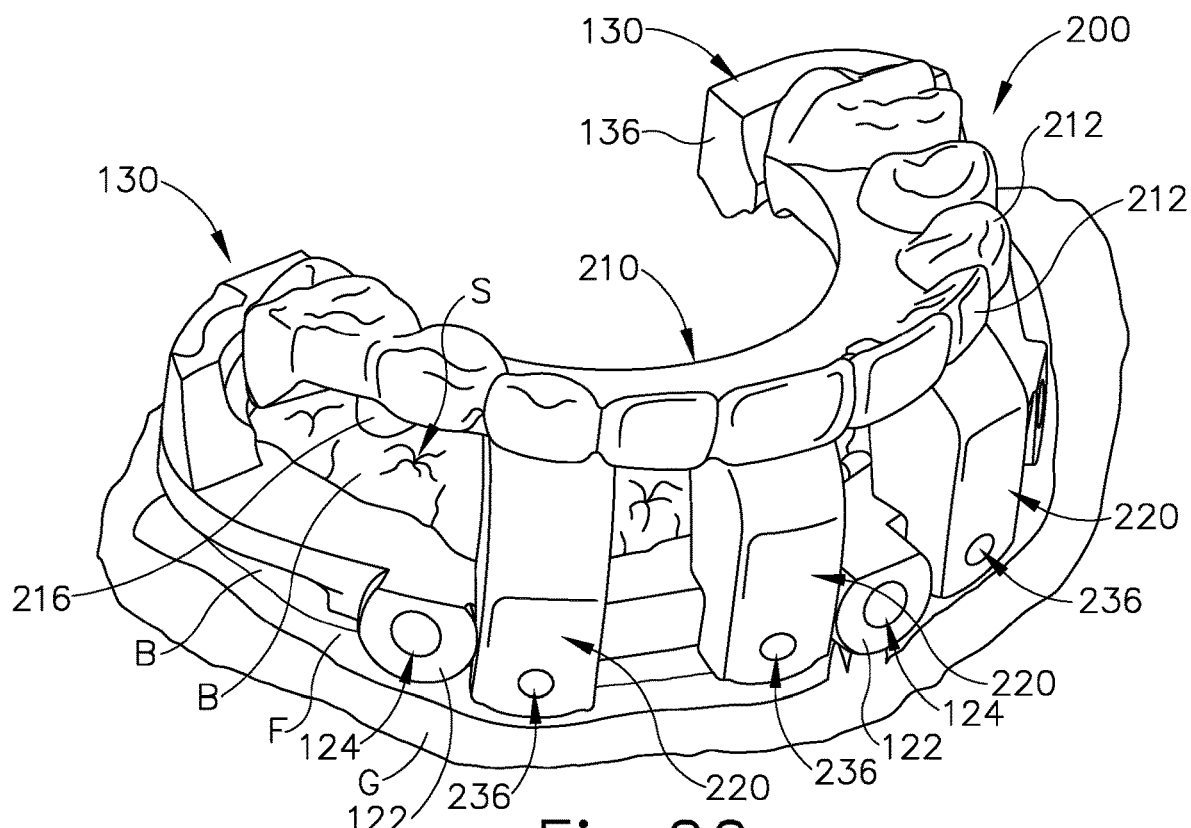
FIG. 20 depicts a perspective view of the assembled combination of the strut assembly of FIG. 4 and the bone foundation guide of FIG. 1 mounted to the alveolar ridge of FIG. 19, before the bone reduction procedure.
Figure 21:
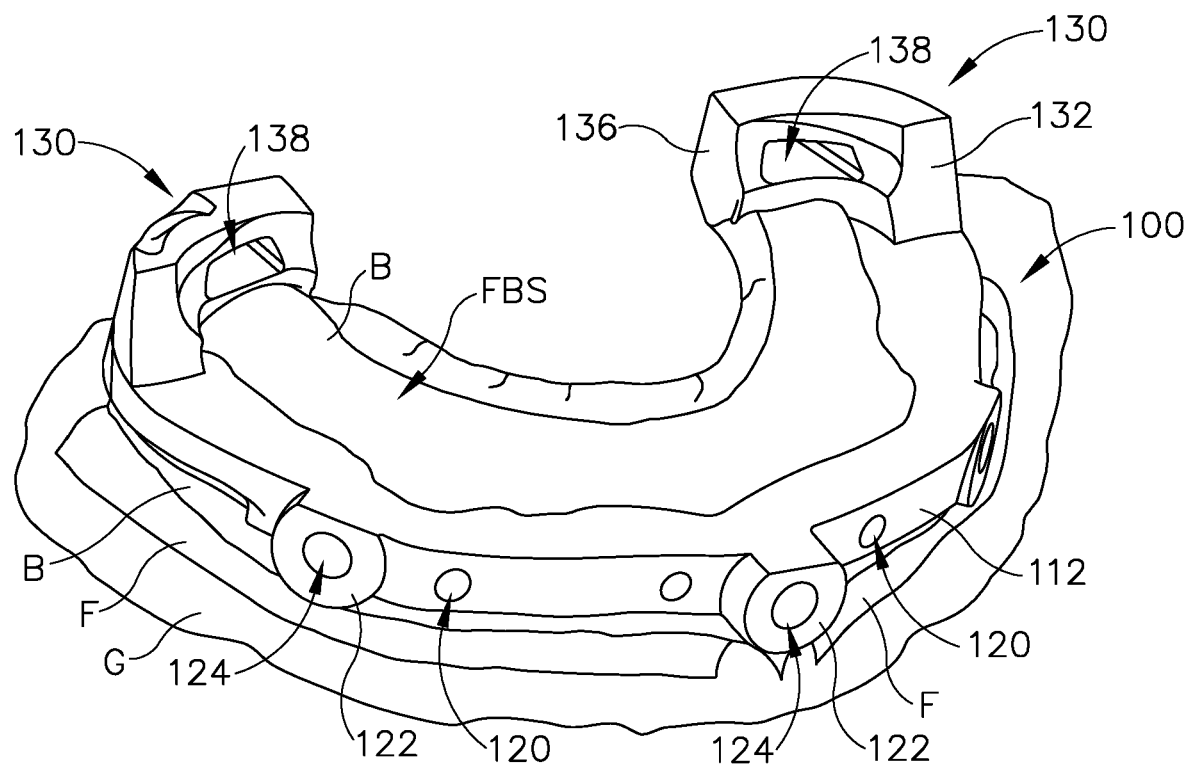
FIG. 21 depicts a perspective view of the bone foundation guide of FIG. 1 mounted to the alveolar ridge of FIG. 19, after the bone reduction procedure.

After securing bone foundation guide (100) to bone as shown in FIG. 19, the surgeon may remove the remaining teeth (T) using any suitable techniques. The surgeon may then secure strut assembly (200) to bone foundation guide (100) as shown in FIG. 20. As noted above, this may include inserting tabs (214) of strut assembly (200) into corresponding slots (138) of bone foundation guide (100). This also includes engaging horizontal body portion (110) with strut members (220), such that shelf portions (230) of strut members (220) receive horizontal body portion (110). At this stage, passageways (236) of strut members (220) are aligned with passageways (122) of horizontal body portion (110). The surgeon may thus insert pins, screws, or other fastener devices through passageways (122, 236) to thereby secure strut assembly (200) to bone foundation guide (100). Also at this stage, studs (216) engage bone (B) at respective points along the alveolar ridge, thereby providing additional stability to strut assembly (200). Contact between studs (216) and bone (B) may further ensure the appropriate vertical and lateral positioning of strut assembly (200) relative to the alveolar ridge.

With strut assembly (200) coupled with bone foundation guide (100), the surgeon may establish a state of occlusion between teeth (210) of strut assembly (200) and the teeth of the opposing alveolar ridge of the patient. This may be done as a preview to confirm that the teeth of the planned prosthetic will be an appropriate fit for the patient, since teeth (210) of strut assembly (200) match the placement and configuration of the teeth of the planned prosthetic. After confirming the appropriate fit, the surgeon may remove strut assembly (200) from bone foundation guide (100).

After strut assembly (200) is removed from bone foundation guide (100), the physician may perform a bone reduction procedure on the alveolar ridge. This may include using a conventional bur or other cutting instrument to remove all portions of the bone (B) that protrudes above the upper surface (116) of bone foundation guide (100). In some instances, the physician may add material to bone (B). Such added material may be formed in part by bone material that has just been removed from the alveolar ridge. In either case, the end result of such procedures may look similar to the state shown in FIG. 21, in which a flush bone surface (FBS) is established. This flush bone surface (FBS) is substantially coplanar with the upper surface (116) of bone foundation guide (100), such that bone foundation guide (100) serves as a bone reduction guide. To achieve this flush bone surface (FBS), the surgeon may use upper surface (116) to provide a visual cue, and in some cases structural support, for the instrumentation that is used to remove the bone (B) protruding above upper surface (116) and/or for the instrumentation that is used to add material to the bone (B) to achieve a flat, planar flush bone surface (FBS). Bone foundation guide (100) may thus provide structural and/or visual guidance for instrumentation during a bone reduction procedure. Bone foundation guide (100) may also provide structural and/or visual guidance for a bone augmentation procedure. The degree of bone reduction and bone augmentation that is required may vary patient to patient, depending on the extent to which bone reduction and bone augmentation is required along the alveolar arch in order to achieve a flat, planar flush bone surface (FBS) that is flush with upper surface (116).

Figure 22:
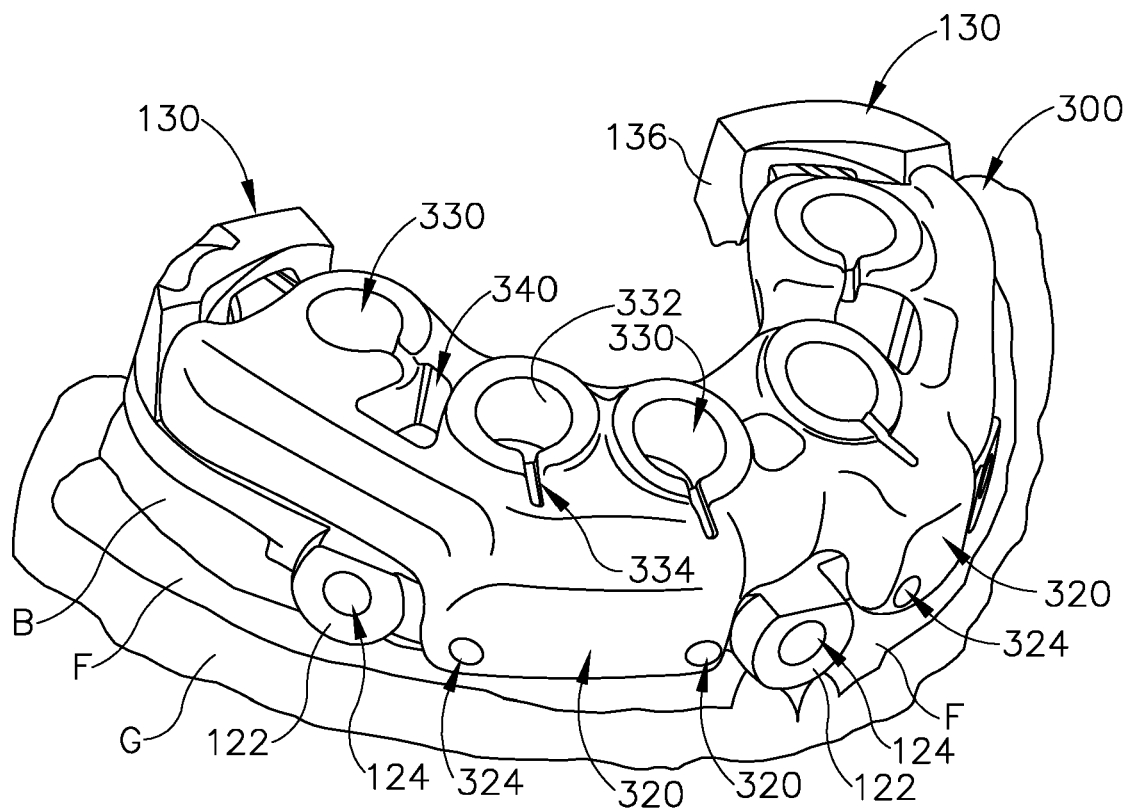
FIG. 22 depicts a perspective view of the assembled combination of the strut assembly of FIG. 4 and the surgical guide of FIG. 11 mounted to the alveolar ridge of FIG. 21.
Figure 23:
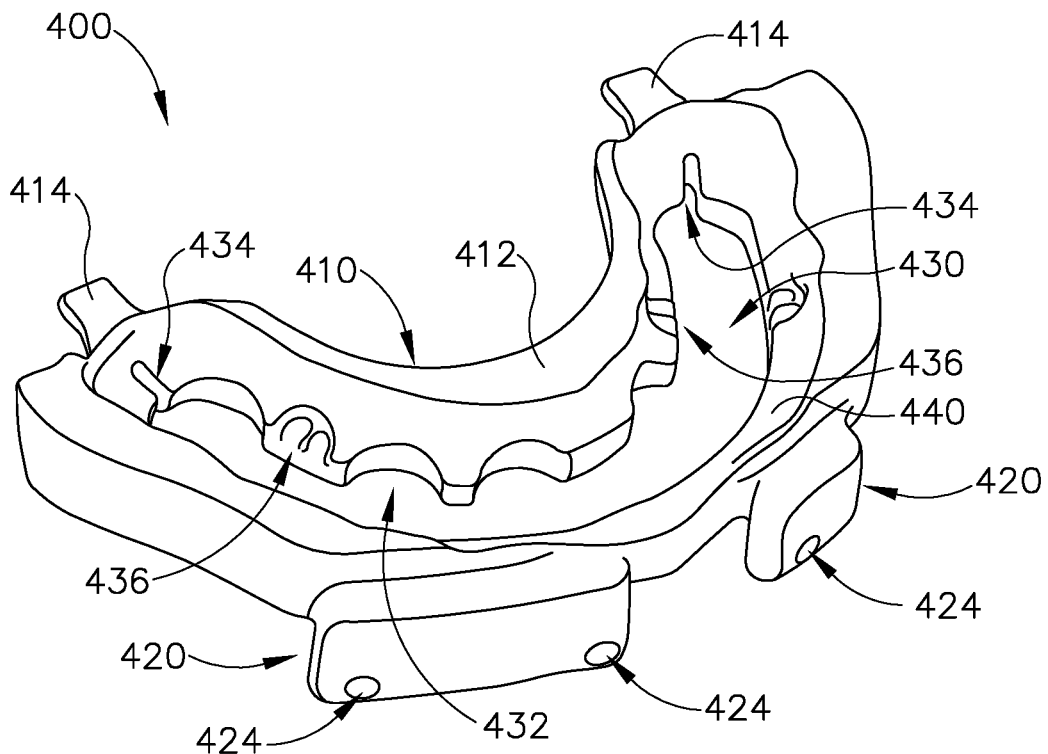
FIG. 23 depicts a perspective view of an exemplary alternative surgical guide.
Figure 24:
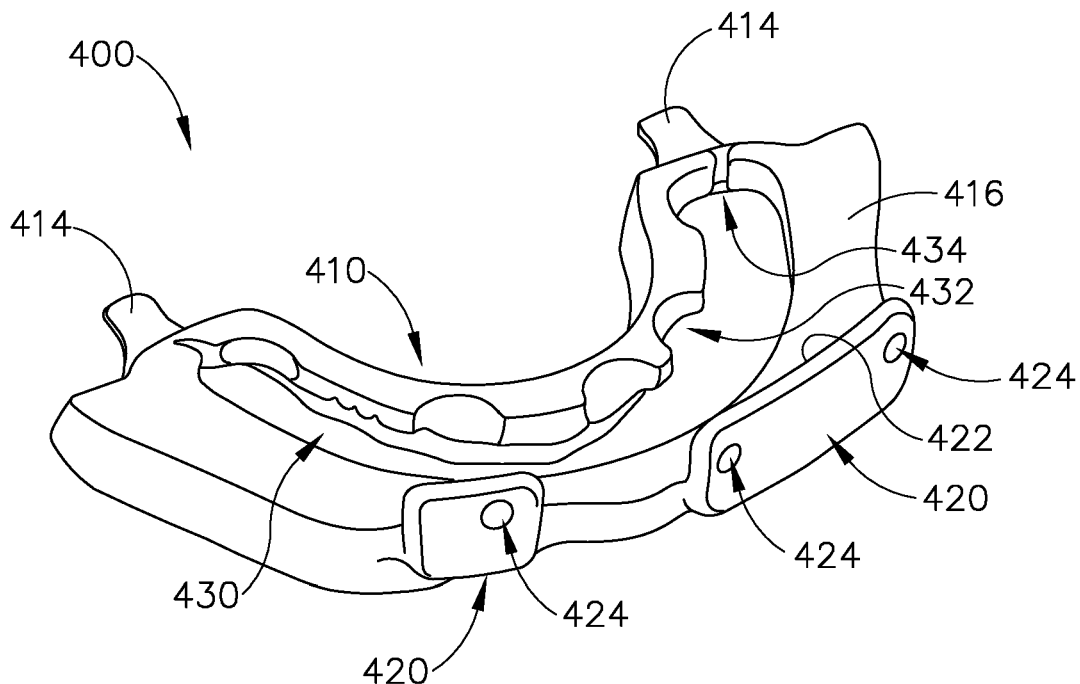
FIG. 24 depicts another perspective view of the surgical guide of FIG. 23.
Figure 25:
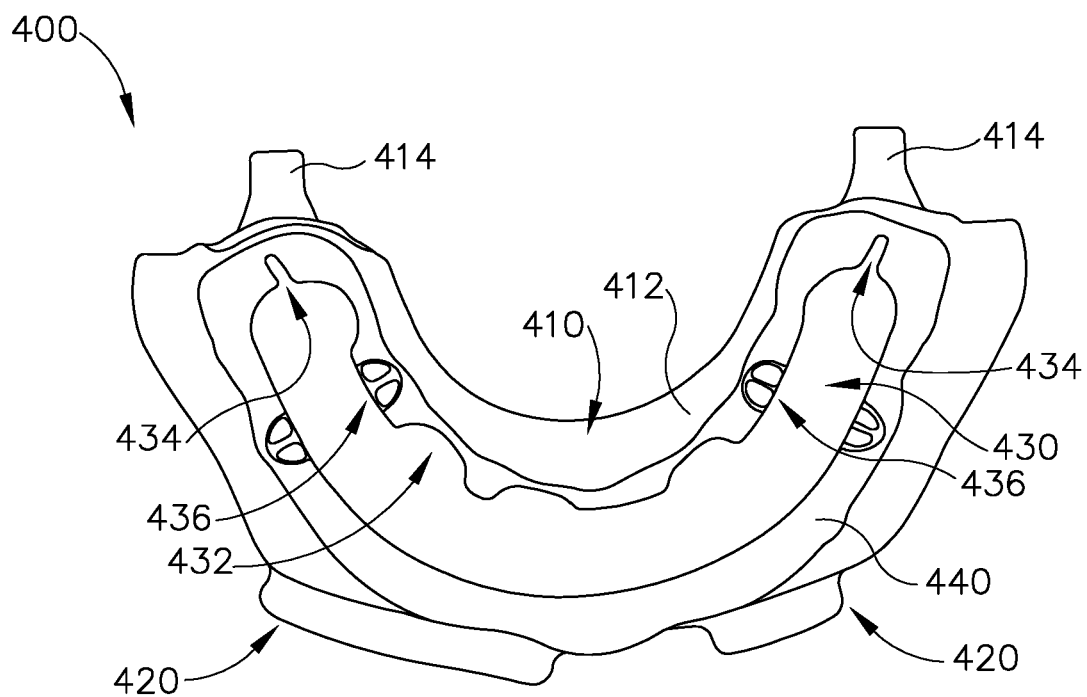
FIG. 25 depicts a top plan view of the surgical guide of FIG. 23.
Figure 26:
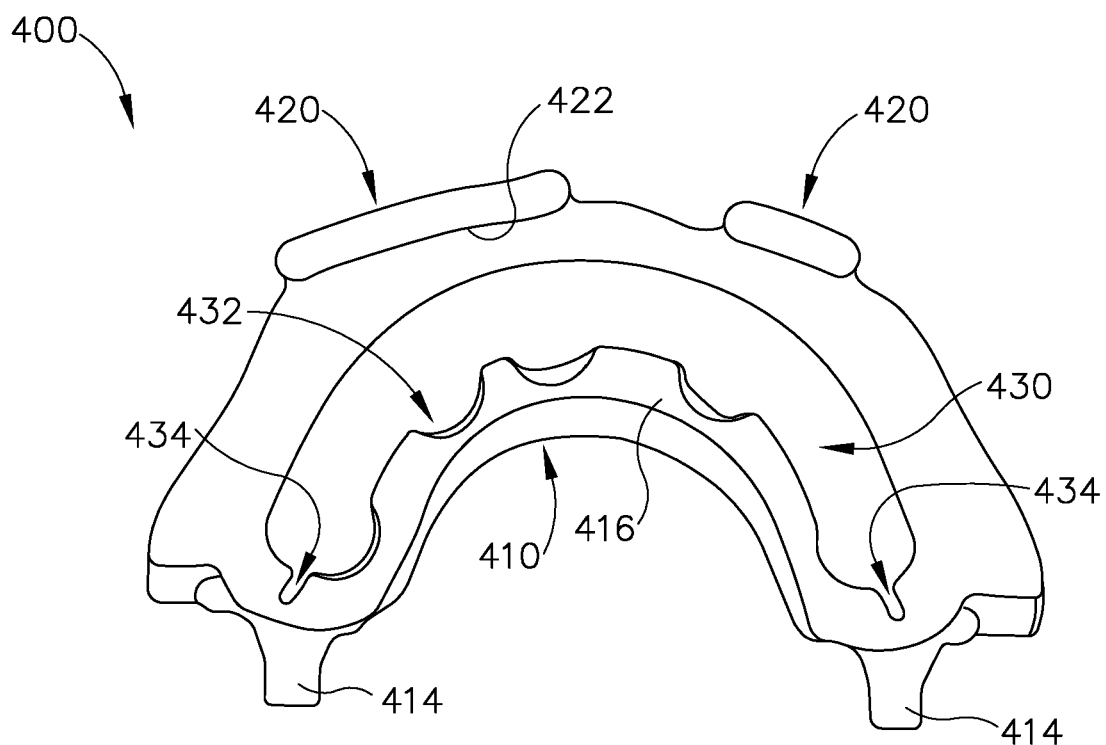
FIG. 26 depicts a bottom plan view of the surgical guide of FIG. 23.
Figure 27:
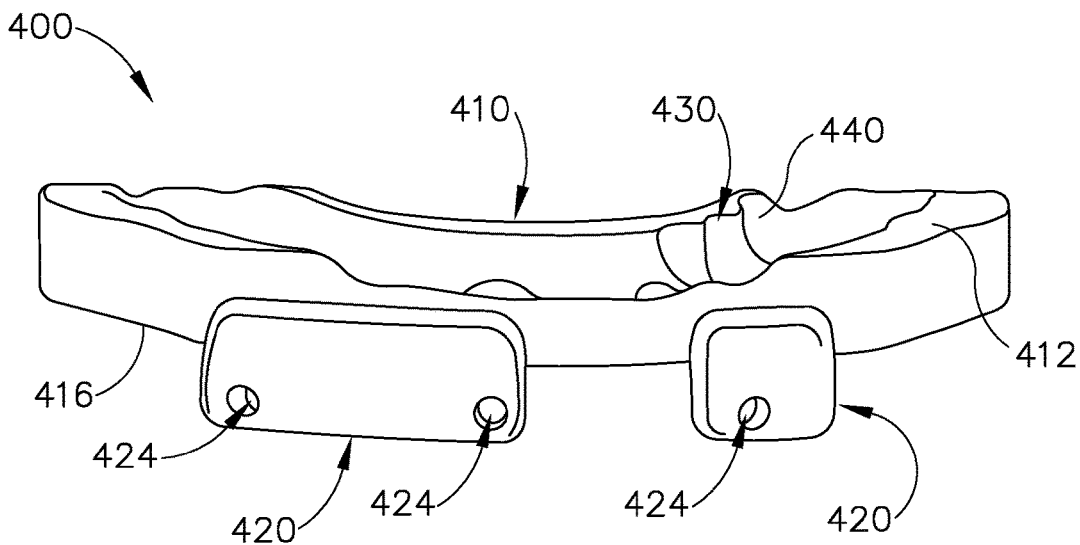
FIG. 27 depicts a front elevation view of the surgical guide of FIG. 23.

After completing the bone reduction (and perhaps bone augmentation) procedure, the surgeon may couple surgical guide (300) with bone foundation guide (100), as shown in FIG. 22. As noted above, this may include inserting tabs (314) of surgical guide (300) into corresponding slots (138) of bone foundation guide (100). This also includes engaging upper surface (116) of horizontal body portion (110) with bottom surface (316) of horizontal body portion (310); and rear facing surfaces (322) of flange members (320) with front surface (112) of horizontal body portion (110). At this stage, passageways (324) of flange members (320) are aligned with passageways (122) of horizontal body portion (110). The surgeon may thus insert pins, screws, or other fastener devices through passageways (122, 324) to thereby secure surgical guide (300) to bone foundation guide (100).

After surgical guide (300) and bone foundation guide (100) are coupled together, the surgeon may insert a drill or other instrument successively in each passageway (330) to form openings in bone (B) to receive implants. The surgeon may then insert the implants and associated installation instrumentation through passageways (330) to install the implants. After the implants are installed, the surgeon may install abutments on the implants, again via passageways (330). After the abutments are installed, the surgeon may remove surgical guide (300) and bone foundation guide (100) from the alveolar arch.

In some versions of the procedure, before or after the implants and abutments are installed, the surgeon may also position a tissue-spacing gasket about the implants and abutments and then secure a temporary prosthetic to the abutments, with the tissue-spacing gasket being configured to mimic the thickness of the gum (G) tissue forming flaps (F). Such a tissue-spacing gasket and temporary prosthetic may be configured and operable in accordance with the teachings of any of the various patent references cited herein. The surgeon may eventually remove the tissue-spacing gasket and temporary prosthetic, bring the flaps (F) back over the alveolar ridge and stitch the gum (G) tissue around the abutments, and then secure the final prosthetic to the abutments. Again, this may be performed in accordance with the teachings of any of the various patent references cited herein.

V. Exemplary Freehand Surgical Guide

In some instances, a physician may wish to use an alternative form of surgical guide (300). By way of example only, a physician may wish to rely more on their own ad hoc personal judgment, and less on the structural guidance provided by passageways (330) to determine the location, orientation, and depth of insertion, etc. for a drill that is used to form openings in the flush bone surface (FBS) that has been established using bone foundation guide (100). Similarly, a physician may wish to rely more on their own ad hoc personal judgment, and less on the structural guidance provided by passageways (330), guide notches (334), and top surfaces (336), to determine the location, orientation, and depth of insertion, etc. for implants and abutments that are secured to the alveolar ridge after the corresponding openings have been formed in the flush bone surface (FBS). FIGS. 23-29 show an exemplary alternative surgical guide (400) that may be used in such instances. Surgical guide (400) may be used with bone foundation guide (100), as a substitute for surgical guide (300), in the procedure described above.

Surgical guide (400) of the present example comprises a horizontal body portion (410) and a set of flange members (420). Horizontal body portion (410) extends along a horizontal plane and defines an arcuate shape corresponding to an alveolar arch of a patient, as described herein. A guide opening (430) is formed through horizontal body portion (410) and follows the same arch as horizontal body portion (410). Guide opening includes a plurality of guide notches (432). Each guide notch (432) is positioned to correspond with the predetermined location of an implant and abutment that will be installed in the alveolar ridge. In the present example, guide notches (432) are only formed in the lingual side of horizontal body portion (410). In other versions, guide notches (432) may be formed in the buccal side of body portion (410) in addition to, or in lieu of, being formed in the lingual side of horizontal body portion. Each terminal end of guide opening (430) includes a slot (434).

Guide opening (430) also includes a set of marker features (436). Marker features (436) are formed in two separate opposing pairs, with one marker feature (436) of each pair being positioned on the lingual side of horizontal body portion (410) and the other marker feature (436) of each pair being positioned on the buccal side of body portion (410). Like guide notches (432), marker features (436) may provide a visual reference to the surgeon, generally indicating the predetermined location of an implant and abutment that will be installed in the alveolar ridge. Guide notches (432) and marker features (436) may thus be regarded as being functionally interchangeable in some instances. The surgeon may thus visually observe the location of guide notches (432) and marker features (436) and drill in the corresponding location to form openings in the bone (B) of the alveolar ridge to receive the dental implants. Some variations of surgical guide (400) may include only guide notches (432) to provide visual guidance to the surgeon, indicating the general location of an implant and abutment that will be installed in the alveolar ridge. Some other variations of surgical guide (400) may include only marker features (436) to provide visual guidance to the surgeon, indicating the general location of an implant and abutment that will be installed in the alveolar ridge. Other variations may include a combination of guide notches (432) and marker features (436). Still other variations may include any other kind(s) of feature(s) that is/are configured to provide visual guidance to the surgeon, generally indicating the predetermined location of an implant and abutment that will be installed in the alveolar ridge. Numerous suitable variations of such visual guidance features will be apparent to those skilled in the art in view of the teachings herein.

A recessed surface in the form of a contoured concave surface (440) extends from top surface (412) of body portion (410), defining the perimeter of guide opening (430). By providing contoured concave surface (440) around guide opening (430), surgical guide (400) provides enhanced visualization of the surgical site in guide opening (430) when surgical guide (400) is positioned over the alveolar ridge. The configuration of contoured concave surface (400) also provides better access for instruments to reach the surgical site in guide opening (430) when surgical guide (400) is positioned over the alveolar ridge, accommodating a variety of instrument end effector sizes and orientations. In some other versions, a flat tapered surface is provided instead of contoured concave surface (440). Other suitable configurations and alternatives will be apparent to those skilled in the art in view of the teachings herein.

A pair of tabs (414) extend proximally from each free end of the arc formed by horizontal body portion (410). Tabs (414) provide structures for coupling surgical guide (400) with bone foundation guide (100) as described in greater detail below. Surgical guide (400) includes two flange members (420) in this example, though surgical guide (400) may instead include more or fewer than two flange members (420). One flange member (420) includes two passageways (424) while the other flange member (420) includes only one passageway (424) in this example. Each flange member (420) includes a rear facing surface (422). Flange members (420) are positioned along the distal or buccal side of body portion (410) and are thereby positioned to engage front surface (112) of bone foundation guide (100) as will be described in greater detail below.

By way of example only, surgical guide (400) may be formed using rapid prototyping equipment (e.g., 3D printing or other additive manufacturing, etc.), based on a three-dimensional digital model as noted above. By way of further example only, surgical guide (400) may be formed of plastic, metal, other materials, and combinations thereof. Various suitable ways in which surgical guide (400) may be formed will be apparent to those skilled in the art in view of the teachings herein.

Figure 28:
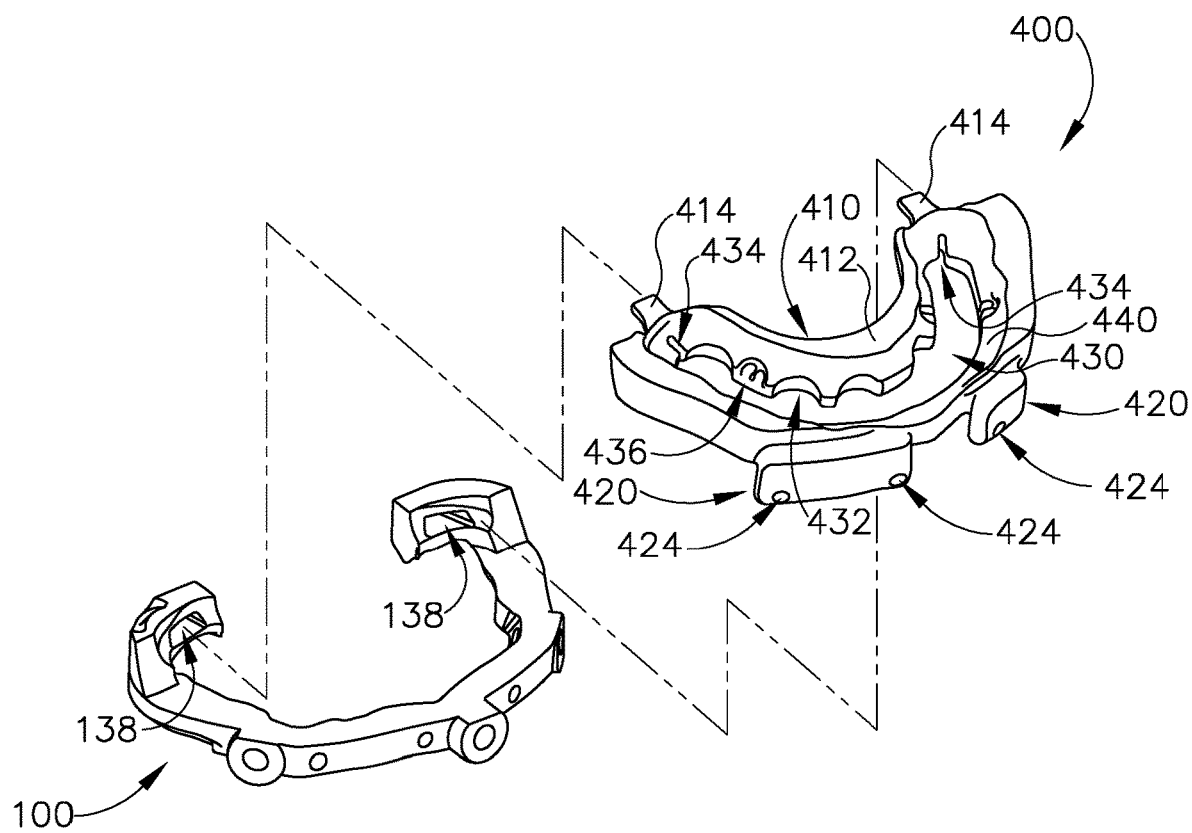
FIG. 28 depicts an exploded perspective view of a combination of the bone foundation guide of FIG. 1 and the surgical guide of FIG. 23.
Figure 29:
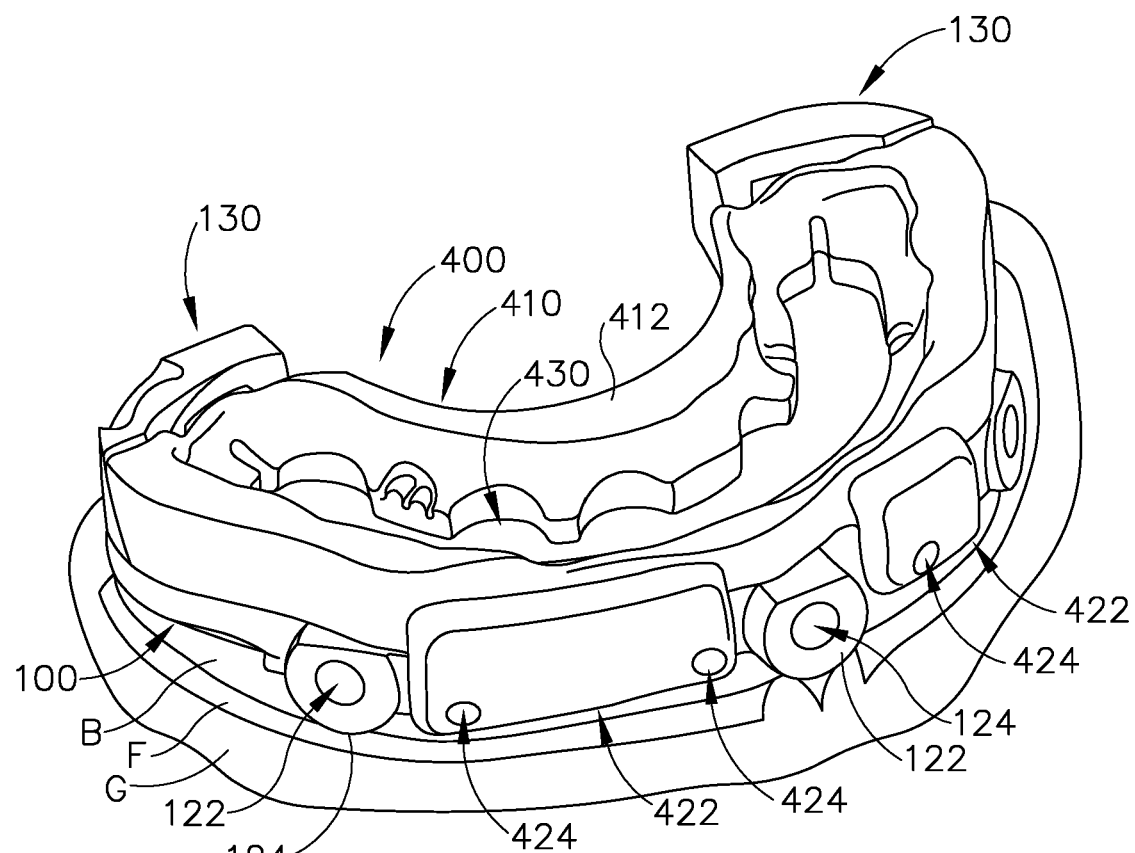
FIG. 29 depicts a perspective view of the surgical guide of FIG. 23 assembled with the bone foundation guide of FIG. 1 mounted to the alveolar ridge of FIG. 21.

FIGS. 28-29 show how surgical guide (400) and bone foundation guide (100) may be coupled together. As shown, tabs (414) of surgical guide (400) may be inserted into corresponding slots (138) of bone foundation guide (100). Bottom surface (416) of horizontal body portion (410) of surgical guide (400) rests atop upper surface (116) of horizontal body portion (110) of bone foundation guide (100). Each rear facing surface (422) of each flange member (420) engages front surface (112) of horizontal body portion (110). Passageways (424) of flange members (420) are aligned with passageways (122) of horizontal body portion (110) when surgical guide (400) is coupled with bone foundation guide (110). When surgical guide (400) and bone foundation guide (100) are coupled together, guide notches (432) are positioned and aligned to visually guide the drilling of openings for implants and the installation of implants in the drilled openings, as described herein.

The procedure in which surgical guide (400) is used is substantially similar to the procedure in which surgical guide (300) is used, as described above. However, instead of relying on the structural support and guidance from passageways (330) and top surfaces (336) of surgical guide (300), the physician will rely on the visual guidance provided by guide notches (432) and/or marker features (436) of surgical guide (400) when drilling implant openings in the bone (B) of the alveolar ridge and installing the implants and abutments in the alveolar ridge. In some variations, a physician may rely on surgical guide (300) when performing the drilling process, then replace surgical guide (300) with surgical guide (400) when performing the implant process and abutment installation process. As yet another merely illustrative example, a physician may rely on surgical guide (400) when performing the drilling process, then replace surgical guide (400) with surgical guide (300) when performing the implant process and abutment installation process. To facilitate such use or otherwise facilitate physician choice, the physician may be provided with a kit that contains surgical guide (300) and surgical guide (400). Such a kit may also include bone foundation guide (100) and strut assembly (200), as well as implant and abutment assemblies (450) as described below.

Figure 30:
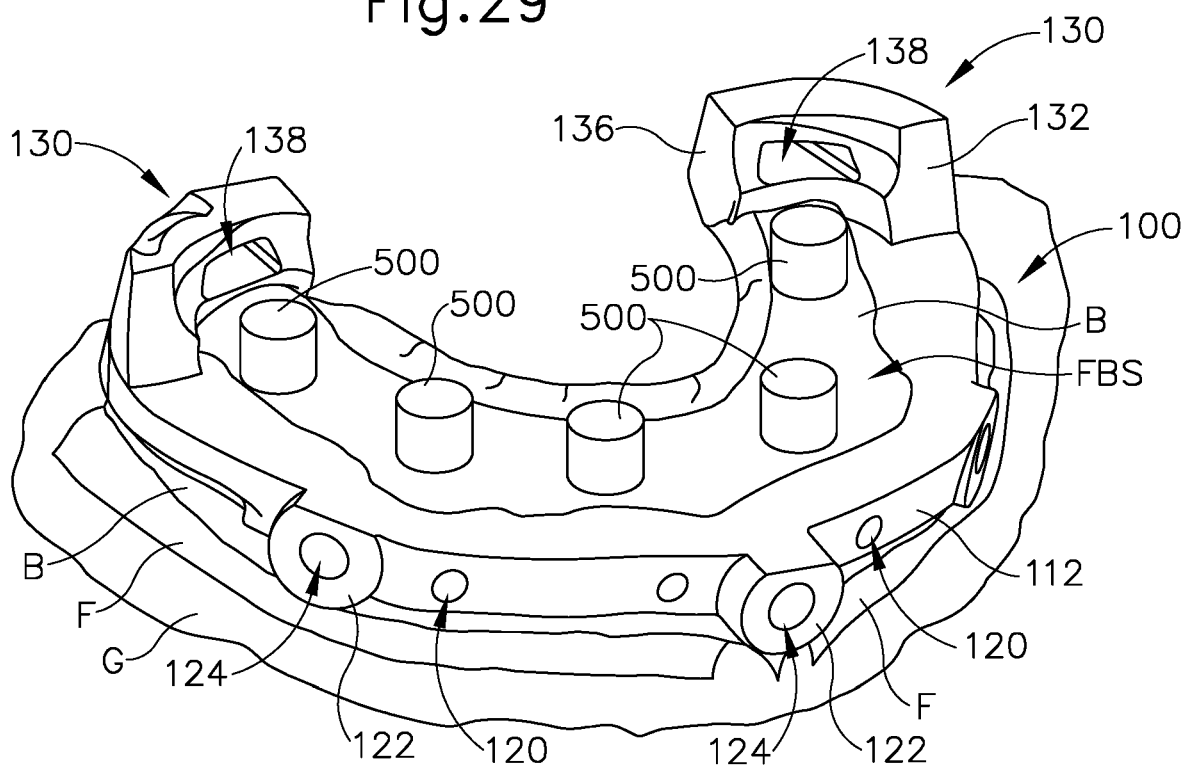
FIG. 30 depicts a perspective view of the alveolar ridge of FIG. 21 with a plurality of implant and abutment assemblies secured therein.

Regardless of whether surgical guide (300) and/or surgical guide (400) is used to guide the drilling process, implant process, and abutment installation process, the final result may appear similar to what is shown in FIG. 30. As shown in FIG. 30, surgical guide (300, 400) has been removed from bone foundation guide (100), and implant and abutment assemblies (450) are left installed in the bone (B) of the alveolar ridge. While implant and abutment assemblies (450) are shown in schematic form in FIG. 30, various suitable forms that implant and abutment assemblies (450) may take will be apparent to those skilled in the art in view of the teachings herein.

As noted above, a tissue spacing gasket may be placed on the bone (B), with openings being formed through the tissue spacing gasket to accommodate the implant and abutment assemblies (450), to approximate the presence of tissue around the installed implant and abutment assemblies (450). A dental prosthetic may then be positioned over the tissue spacing gasket and the installed implant and abutment assemblies (450) to confirm that the dental prosthetic will properly receive the implant and abutment assemblies; and to confirm that the dental prosthetic is otherwise properly configured for the patient. If the configuration is confirmed as appropriate, the dental prosthetic and tissue spacing gasket are removed. The flaps (F) of gum (G) are positioned back over the bone (B) and around the installed implant and abutment assemblies (450) and are then sutured in place. After the gum (G) sufficiently heals, the dental prosthetic is secured to implant and abutment assemblies (450), on top of the healed gum (G) tissue.

VI. Exemplary Spacing Gasket

As noted above, a surgeon may position a tissue-spacing gasket over the flush bone surface (FBS) that has been established using bone foundation guide (100). The tissue-spacing gasket may have a thickness that is configured to mimic the thickness of the gum (G) tissue forming flaps (F). The tissue-spacing gasket may also have openings that are configured to receive corresponding implant and abutment assemblies (450). The surgeon may place a prosthetic over the installed implant and abutment assemblies (450), and on top of the tissue-spacing gasket, to confirm that the prosthetic will provide an appropriate fit after being fully installed. The tissue-spacing gasket may thus serve a function of properly positioning a prosthetic over an alveolar arch; and ensuring that the prosthetic will ultimately fit appropriately after being installed.

In addition, a tissue-spacing gasket may prevent certain surfaces from coming into contact with a dental adhesive during a "pickup process," where a prosthetic is secured to an abutment with the adhesive while in the patient's mouth. For instance, as will be described in greater detail below, an abutment of an implant abutment assembly (450) may include an undercut region that is filled by a tissue spacing gasket, such that the gasket prevents the adhesive from reaching the undercut region of the abutment. A tissue spacing gasket may also prevent the adhesive from reaching the bone (B) and gum (G) tissue of the alveolar ridge. To complete the pickup process after the adhesive has sufficiently cured, the surgeon may unscrew the abutment from the implant of the implant abutment assembly (450), then lift the combination of the prosthetic and abutment off of the tissue spacing gasket.

After confirming the proper fit of a prosthetic and completing a pickup process, the surgeon may remove the tissue-spacing gasket, bring the flaps (F) back over the alveolar ridge and stitch the gum (G) tissue around the abutments. In some cases, it may be necessary to allow the stitched flaps (F) to heal before completing final installation of the prosthetic. Either way the prosthetic may eventually be permanently secured to the alveolar ridge via implant abutment assemblies (450).

In procedures where a surgical guide like surgical guide (300) is used, the tissue-spacing gasket may have a precisely predetermined shape, with the openings being precisely located at predetermined locations that correspond to the locations of passageways (330) since it is known that the implant and abutment assemblies will ultimately be positioned at these locations. However, in procedures where a surgical guide like surgical guide (400) is used, the surgeon has greater flexibility and discretion in deciding where exactly the implant and abutment assemblies will be installed in the alveolar ridge. Thus, it may be desirable to provide an alternative kind of tissue-spacing gasket that provides flexibility in positioning, allowing the gasket to be more easily positioned at various locations along the alveolar ridge, depending on where exactly the surgeon decides to install the implant and abutment assemblies. Examples of such a tissue-spacing gasket and gasket assembly are described in greater detail below. While these examples are provided in the context of a procedure where surgical guide (300) is used, it should be understood that these examples of a tissue-spacing gasket and gasket assembly may also be used in procedures where surgical guide (400) is used. The following examples are thus not necessarily limited to use in procedures where surgical guide (300) is used.

Figure 31:
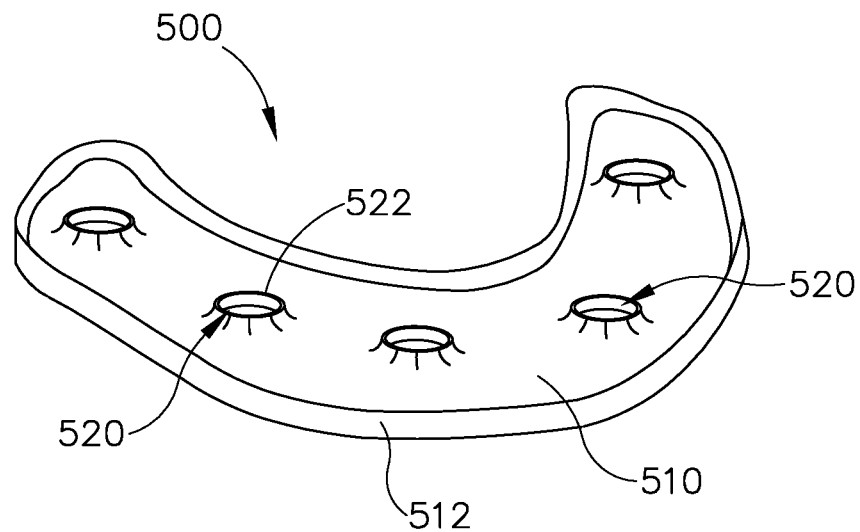
FIG. 31 depicts a perspective view of an exemplary spacing gasket.

FIG. 31 shows an exemplary spacing gasket (500) that includes an arcuate body (510) with a plurality of openings (520) formed therethrough. In some versions, body (510) is formed of silicone, though any other suitable material may be used. Body (510) includes an upwardly projecting outer lip (512) extending around the outer perimeter of body (510). Body (510) further includes an upwardly projecting annular lip (522) extending around each opening (520). In some versions, body (510) defines a concave recess between lips (512, 522), like the configuration shown in FIG. 32 as described in greater detail below. By way of example only, each lip (512, 522) may have a thickness of approximately 3 mm while the thinnest region of body (510) (i.e., between lips (512, 522) may have a thickness of approximately 1 mm. Alternatively, any other suitable thicknesses may be used.

The shape of arcuate body (510) is configured to correspond with the arcuate shape of the alveolar arch of the patient. The thickness of arcuate body (510) is configured to mimic the thickness of the gum (G) tissue forming flaps (F). Openings (520) of the present example are positioned to correspond with locations where implant and abutment assemblies (450) are to be installed in the alveolar arch. In the context of surgical guide (430), the location of openings (520) may generally correspond with the location of guide notches (432) and/or marker features (436).

Figure 32:
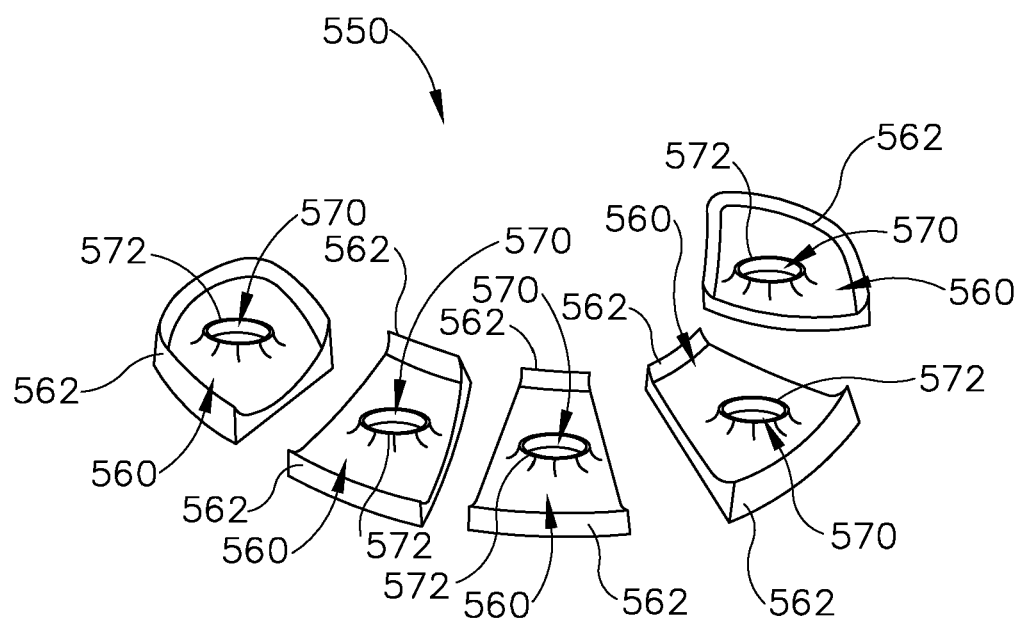
FIG. 32 depicts a perspective view of an exemplary spacing gasket assembly formed by pieces of the spacing gasket of FIG. 31.

While openings (520) are positioned to correspond with locations where implant and abutment assemblies (450) are to be installed in the alveolar arch, the ultimate locations of the installed implant and abutment assemblies (450) may slightly vary due to the "freehand" nature of bone drilling procedures where surgical guide (430) is used. To accommodate for potential variation in the ultimate positioning of the installed implant and abutment assemblies (450), spacing gasket (500) may be converted into a spacing gasket assembly (550) as shown in FIG. 32.

Spacing gasket assembly (550) of this example comprises a plurality of bodies (560) that together form an arcuate arrangement generally corresponding to the configuration of body (510) of spacing gasket (500). In some instances, a surgeon is initially provided with spacing gasket (500), then the surgeon cuts spacing gasket (500) to form spacing gasket assembly (550) on an ad hoc basis before positioning bodies (560) on the alveolar ridge. In some other instances, spacing gasket assembly (550) is formed at a manufacturing stage before the surgeon receives spacing gasket assembly (550), such that the surgeon receives spacing gasket assembly (550) instead of receiving gasket (500) and having to cut spacing gasket (500). Each body (560) of spacing gasket assembly (550) includes one outer lip (562) (in the case of the outer-most bodies (560)) or two outer lips (562) corresponding to outer lip (512) of body (510). Each body (560) of spacing gasket assembly (550) also includes one opening (570) corresponding to openings (520). An annular lip (572) surrounds each opening (570), like lips (522).

Figure 33:
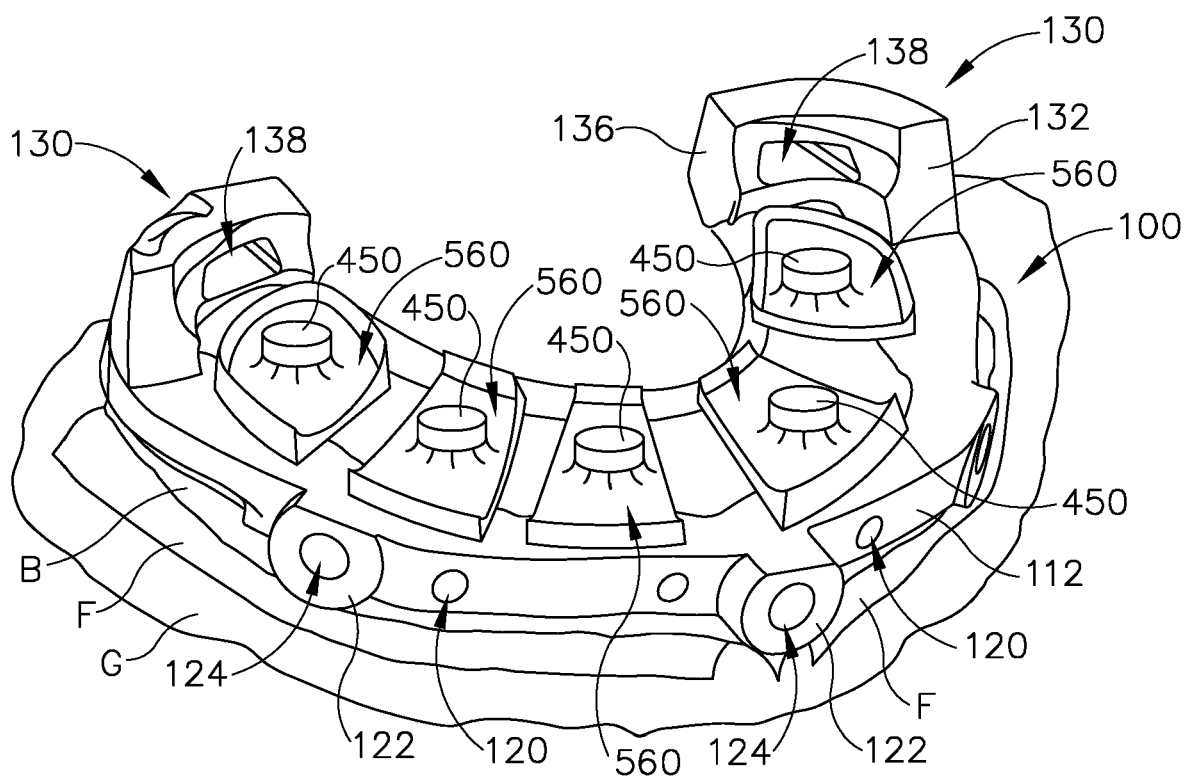
FIG. 33 depicts a perspective view of the spacing gasket assembly of FIG. 33 positioned on the alveolar ridge of FIG. 21, with the implant and abutment assemblies of FIG. 30 positioned in openings of gasket bodies of the spacing gasket assembly.

FIG. 33 shows bodies (560) of spacing gasket assembly (550) positioned on the flat bone surface (FBS) of the alveolar ridge, with implant and abutment assemblies (450) positioned in respective openings (520). In the example shown, bodies (560) are sized such that portions of bodies (560) extend over upper surface (116) of horizontal body portion (110) of bone foundation guide (100). In some other versions, bodies (560) may be sized such that portions of bodies (560) do not extend over upper surface (116) of horizontal body portion (110) of bone foundation guide (100).

Figure 34:
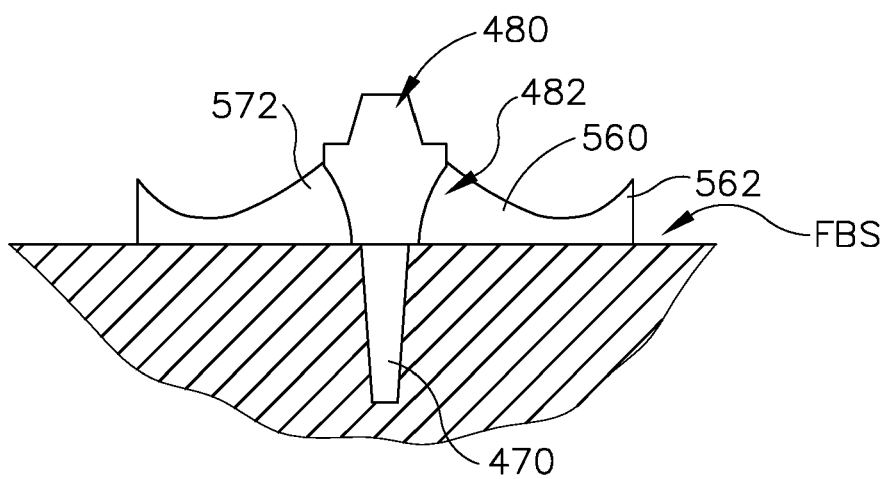
FIG. 34 depicts a cross-sectional view of one of the implant and abutment assemblies of FIG. 30 positioned in an opening of a corresponding gasket body of the spacing gasket assembly of FIG. 33.

FIG. 34 shows an exemplary relationship between a body (560) and a corresponding implant and abutment assembly (450). As shown, implant and abutment assembly (450) includes an implant (470) that is fixedly installed (e.g., via screw threading) into the bone (B) of the alveolar ridge. An abutment (480) (e.g., a multi-unit abutment) is fixedly secured to implant (470) (e.g., via a screw). Abutment (480) includes an undercut region (482). Annular lip (572) extends into undercut region (482), thereby filling undercut region.

In cases where a "pickup process" is used to secure a dental prosthetic to abutment (480) using techniques known in the art, the positioning of annular lip (572) in undercut region (482) may prevent acrylic, cement, or other dental adhesive that is used in the pickup process from entering undercut region (482). The rest of each body (560) may also prevent the acrylic, cement, or other dental adhesive that is used in the pickup process from getting onto the bone (B) and adjacent gum (G) tissue of the alveolar ridge. Moreover, as noted above, the thickness and other configuration characteristics of bodies (560) may mimic the thickness of gum (G) tissue after flaps (F) are later repositioned over the flush bone surface (FBS), thereby ensuring that abutment (480) is properly positioned in the prosthetic during the pickup process.

In some cases, bodies (560) are positioned over abutments (480) after abutments have been installed on the alveolar ridge. In such cases, elastomeric bodies (560) may enable bodies (560) to stretch around abutments (480), with annular lips (572) resiliently contracting to fill undercut regions (482) once bodies (560) are properly seated. In some other cases, implants (470) are installed first, then bodies (560) are positioned coaxially in relation to corresponding implants (470), abutments (480) are then positioned over bodies (560) with undercut regions (482) receiving corresponding annular lips (572), and then abutments (480) are secured to implants (470). Other suitable ways in which spacing gasket (500) and gasket assembly (550) may be used will be apparent to those skilled in the art in view of the teachings herein.

VII. Exemplary Dental Prosthetic

Figure 35:
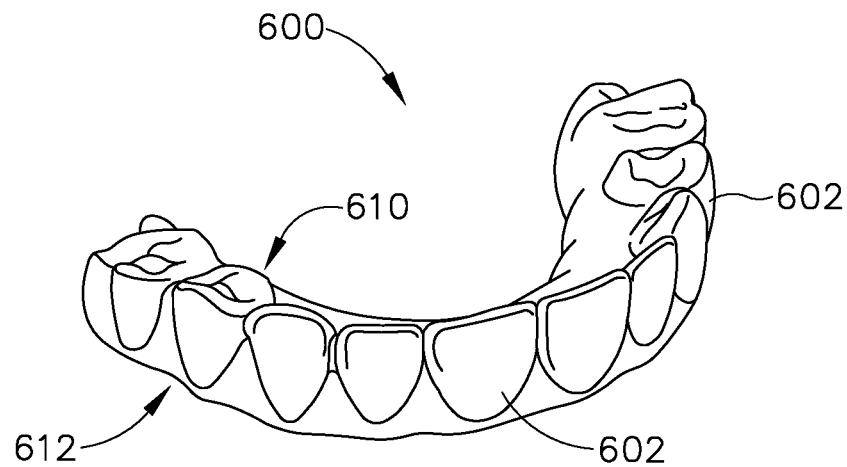
FIG. 35 depicts a perspective view of an exemplary dental prosthetic.
Figure 36:
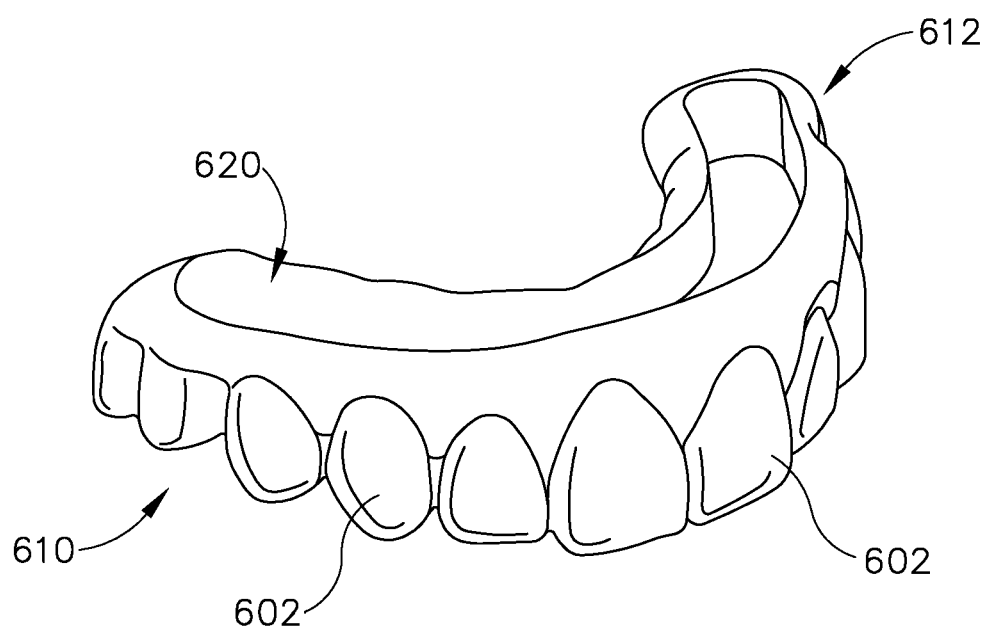
FIG. 36 depicts another perspective view of the dental prosthetic of FIG. 35.
Figure 37:
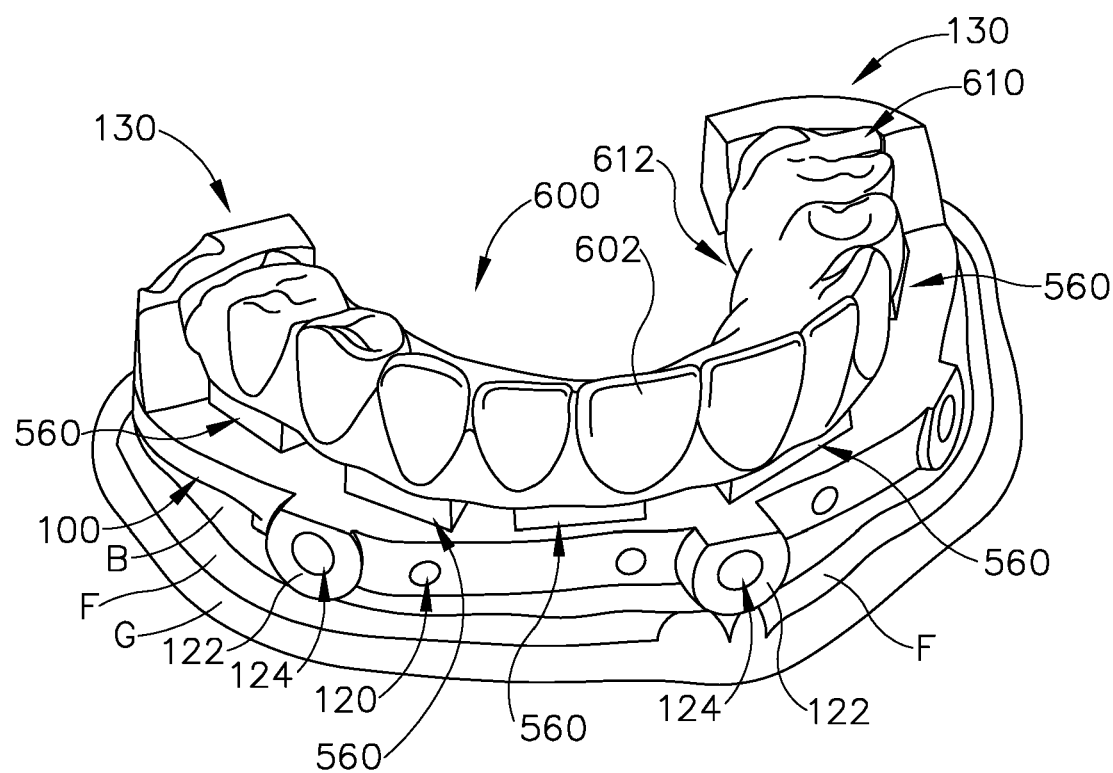
FIG. 37 depicts a perspective view of the dental prosthetic of FIG. 35 and the bone foundation guide of FIG. 1 mounted to assembly of FIG. 33.

In some conventional procedures, a dental prosthetic may have discrete openings formed completely through the dental prosthetic, with such openings enabling the prosthetic to be secured to respective implant and abutment assemblies (450). For instance, the openings may provide a passageway for adhesive to be introduced after the dental prosthetic is positioned over the implant and abutment assemblies (450), thereby allowing the adhesive to reach the space between the abutments of the implant and abutment assemblies (450) and the body of the dental prosthetic. Such openings may intrude into the prosthetic representations of teeth in the dental prosthetic, at least on the lingual side and/or occlusal surface of the dental prosthetic. This may be unsightly and present opportunities for food and other debris to accumulate. Moreover, the presence of these openings may compromise the structural integrity of the dental prosthetic, adversely affecting the long-term reliability of the dental prosthetic. While skilled physicians may be capable of making the presence of such openings and the associated adhesive less obvious to the casual observer of the patient; and provide flush surface transitions between the cured adhesive and the adjacent regions of the dental prosthetic body, it may be desirable to provide an alternative form of dental prosthetic that lacks such openings. FIGS. 35-37 show an example of such an alternative dental prosthetic (600).

In addition to providing the above-noted advantages in some cases, the exemplary dental prosthetic (600) described below may also provide a physician with flexibility to implement dental prosthetic (600) as a screw retained or non-screw retained attachment (e.g., like an overdenture attachment). By way of further example only, dental prosthetic (600) may be utilized in a "pickup process," where dental prosthetic (600) is picked up in acrylic, dental cement, or some other dental adhesive with a non-screw retained overdenture attachment feature. In some such cases, at a later date after the gum (G) tissue of the patient heals, dental prosthetic (600) may be converted to a screw retained attachment by removing the overdenture attachment feature from dental prosthetic (600); then adding screws to the secure dental prosthetic (600) to the desired abutments of the implant and abutment assemblies (450). In some such cases, openings may need to be formed through dental prosthetic (600) to allow screws to pass through dental prosthetic (600)

Dental prosthetic (600) of the present example comprises a horizontally extending body (610) that forms an arch that is configured to match the alveolar arch of the patient in which dental prosthetic (600) is to be installed. Dental prosthetic (600) further includes a full set of representations (602) of teeth. The underside (612) of body (610) includes an arcuate trough (620). Trough (620) is configured to receive implant and abutment assemblies (450) and adhesive, providing substantial space around the implant and abutment assemblies (450) to receive adhesive for bonding dental prosthetic (600) to implant and abutment assemblies (450). The physician may thus introduce adhesive to trough (620) and then position dental prosthetic (600) over installed implant and abutment assemblies (450). Once the adhesive cures, dental prosthetic (600) may deemed permanently installed on the alveolar ridge.

By way of example only, dental prosthetic (600) may be formed using rapid prototyping equipment (e.g., 3D printing or other additive manufacturing, etc.), based on a three-dimensional digital model as noted above. Various suitable ways in which dental prosthetic (600) may be formed will be apparent to those skilled in the art in view of the teachings herein.

As shown in FIG. 37, dental prosthetic (600) may be placed on gasket bodies (560) over the patient's alveolar arch while bone foundation guide (100) is installed on the alveolar arch. This may be done to ensure that the installed implant and abutment assemblies (450) will be appropriately received in trough (620), that dental prosthetic (600) will otherwise properly fit over the alveolar arch, and that representations (602) of teeth will achieve the desired occlusal fit with the teeth of the opposing occlusal arch. As described above, gasket bodies (560) are configured to mimic the thickness of gum (G) tissue after flaps (F) are repositioned over the flush bone surface (FBS). In some other scenarios, flaps (F) are first repositioned over the flush bone surface (FBS) and secured in place around implant and abutment assemblies (450), and dental prosthetic (600) is then placed over the re-secured flaps (F), such that the tissue spacing gasket (500) or gasket assembly (550) may be omitted.

To the extent that the physician is satisfied with the fit of dental prosthetic (600) at the stage shown in FIG. 37, the physician may remove bone foundation guide (100) and gasket bodies (560); and ultimately secure dental prosthetic (600) in place on implant and abutment assemblies (450) via adhesive disposed in trough (620). Dental prosthetic (600) may then be permanently secured in place. Alternatively, as described above, dental prosthetic (600) may be secured to the alveolar ridge via an overdenture attachment positioned in trough (620). Various suitable forms that such an overdenture attachments may take will be apparent to those skilled in the art in view of the teachings herein. As yet another merely illustrative example, dental prosthetic (600) may be secured to implant and abutment assemblies (450) via one or more screws, using any techniques as may be apparent to those skilled in the art in view of the teachings herein.

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising a first guide member, the first guide member comprising: (i) a horizontal body portion, wherein the horizontal body portion has an arcuate configuration, wherein the horizontal body portion includes: (A) a first horizontal surface, wherein the first horizontal surface is flat, (B) a front surface, (C) a rear surface, wherein the rear surface is configured to closely mate with a front-facing bone structure of an alveolar arch of a patient, and (D) a second horizontal surface, wherein the front and rear surfaces extend between the first and second horizontal surfaces, (ii) a first upright body portion positioned at one end of the horizontal body portion, wherein the first upright body portion includes a first inwardly extending portion, wherein a first engagement surface of the first inwardly extending portion is configured to rest on a ridge of the alveolar arch of the patient, and (iii) a second upright body portion positioned at another end of the horizontal body portion, wherein the second upright body portion includes a second inwardly extending portion, wherein a second engagement surface of the second inwardly extending portion is configured to rest on a ridge of the alveolar arch of the patient, wherein the first guide member lacks a component configured to extend along a lingual or palatal side of the alveolar arch of the patient.

Example 2

The apparatus of Example 1, wherein the first upright body portion defines a first slot, wherein the second upright body portion defines a second slot.

Example 3

The apparatus of any one or more of Examples 1 through 2, wherein the horizontal body portion defines a plurality of openings extending from the front surface to the rear surface.

Example 4

The apparatus of any one or more of Examples 1 through 3, wherein the first engagement surface is configured to closely mate with a first bone structure of the alveolar ridge of the patient, wherein the second engagement surface is configured to closely mate with a second bone structure of the alveolar ridge of the patient.

Example 5

The apparatus of any one or more of Examples 1 through 4, further comprising a strut assembly, wherein the strut assembly comprises: (i) a horizontal body portion, wherein the horizontal body portion of the strut assembly has an arcuate configuration generally corresponding to the arcuate configuration of the first guide member, (ii) a set of strut members configured to engage the horizontal body portion of the first guide member, and (iii) a set of three-dimensional representations of teeth, wherein the strut members are configured to position the teeth at a predetermined distance from the first horizontal surface of the first guide member.

Example 6

The apparatus of Example 5, wherein the strut members include shelf portions, wherein the shelf portions are configured to engage the first horizontal surface and the front surface of the first guide member.

Example 7

The apparatus of any one or more of Examples 5 through 6, wherein the horizontal body portion of the first guide member includes a first set of openings, wherein the strut members include a second set of openings, wherein the second set of openings is configured to align with the first set of openings, wherein the first and second sets of openings are configured to receive fasteners when the second set of openings is aligned with the first set of openings.

Example 8

The apparatus of any one or more of Examples 5 through 7, wherein the horizontal body portion of the strut assembly defines a pair of tabs at each end of the arcuate configuration, wherein the first guide member defines a pair of slots, wherein the slots are configured to receive the tabs.

Example 9

The apparatus of Example 8, wherein the slots are defined by the first and second upright body portions.

Example 10

The apparatus of any one or more of Examples 5 through 9, wherein the strut assembly further includes one or more studs projecting from the horizontal body portion of the strut assembly opposite to the teeth, wherein the studs are configured to engage corresponding regions of the alveolar ridge of the patient.

Example 11

The apparatus of any one or more of Examples 1 through 10, further comprising a second guide member, wherein the second guide member comprises: (i) a horizontal body portion, wherein the horizontal body portion of the second guide member has an arcuate configuration generally corresponding to the arcuate configuration of the first guide member, (ii) a set of flange members configured to engage the horizontal body portion of the first guide member, and (iii) a set of guide passageways.

Example 12

The apparatus of Example 11, wherein the horizontal body portion of the second guide member has a horizontal surface configured to engage the first horizontal surface of the horizontal body portion of the first guide member.

Example 13

The apparatus of any one or more of Examples 11 through 12, wherein each flange member has a rear surface configured to engage the front surface of the horizontal body portion of the first guide member.

Example 14

The apparatus of any one or more of Examples 11 through 13, wherein the horizontal body portion of the first guide member includes a first set of openings, wherein the flange members include a second set of openings, wherein the second set of openings is configured to align with the first set of openings, wherein the first and second sets of openings are configured to receive fasteners when the second set of openings is aligned with the first set of openings.

Example 15

The apparatus of any one or more of Examples 11 through 14, wherein the horizontal body portion of the second guide member defines a pair of tabs at each end of the arcuate configuration, wherein the first guide member defines a pair of slots, wherein the slots are configured to receive the tabs.

Example 16

The apparatus of Example 15, wherein the slots are defined by the first and second upright body portions.

Example 17

The apparatus of claim 1, further comprising a second guide member, wherein the second guide member comprises: (i) a horizontal body portion, wherein the horizontal body portion of the second guide member has an arcuate configuration generally corresponding to the arcuate configuration of the first guide member, (ii) a set of flange members configured to engage the horizontal body portion of the first guide member, and (iii) guide opening, wherein the guide opening has an arcuate configuration extending along a portion of the horizontal body portion of the second guide member.

Example 18

The apparatus of Example 17, wherein the horizontal body portion of the second guide member has a horizontal surface configured to engage the first horizontal surface of the horizontal body portion of the first guide member.

Example 19

The apparatus of any one or more of Examples 17 through 18, wherein each flange member has a rear surface configured to engage the front surface of the horizontal body portion of the first guide member.

Example 20

The apparatus of any one or more of Examples 17 through 19, wherein the horizontal body portion of the first guide member includes a first set of openings, wherein the flange members include a second set of openings, wherein the second set of openings is configured to align with the first set of openings, wherein the first and second sets of openings are configured to receive fasteners when the second set of openings is aligned with the first set of openings.

Example 21

The apparatus of any one or more of Examples 17 through 20, wherein the horizontal body portion of the second guide member defines a pair of tabs at each end of the arcuate configuration, wherein the first guide member defines a pair of slots, wherein the slots are configured to receive the tabs.

Example 22

The apparatus of Example 21, wherein the slots are defined by the first and second upright body portions.

Example 23

The apparatus of any one or more of Examples 17 through 22, wherein the horizontal body portion of the second guide member comprises a flat upper surface and a recessed surface extending from the flat upper surface to the guide opening.

Example 24

The apparatus of Example 23, wherein the recessed surface has a concave contour.

Example 25

The apparatus of any one or more of Examples 17 through 24, further comprising a plurality of guide notches positioned along the guide opening.

Example 26

The apparatus of Example 25, wherein the horizontal body portion of the second guide member includes a buccal portion and a lingual portion, wherein at least one of the guide notches is positioned along the lingual portion.

Example 27

The apparatus of any one or more of Examples 17 through 26, further comprising a plurality of marker features positioned along the guide opening.

Example 28

The apparatus of any one or more of Examples 17 through 27, wherein arcuate configuration of the guide opening terminates at two ends, wherein each end of the guide opening includes a slot.

Example 29

A dental prosthetic, comprising: (a) a body, wherein the body has a horizontally extending arcuate configuration configured to correspond with an alveolar arch of a patient; (b) a plurality of representations of teeth extending from a first side of the body; and (c) a recess extending along a second side of the body, wherein the recess has a horizontally extending arcuate configuration extending along a portion of the arcuate configuration of the body.

IX. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A method comprising:
  (a) positioning a first guide member relative to an alveolar arch of a patient, the first guide member comprising:
    (i) a horizontal body portion, the horizontal body portion having an arcuate configuration, the horizontal body portion including:
      (A) a first surface,
      (B) a second surface, the second surface facing away from a front-facing structure of the alveolar arch of the patient,
      (C) a third surface, the third surface mating with the front-facing structure of the alveolar arch of the patient, and

(D) a fourth surface opposite to the first surface, the second surface and the third surface each extending between the first surface and the fourth surface, (ii) a first upright body portion positioned at a first end of the horizontal body portion such that the first end of the horizontal body portion terminates at the first upright body portion, the first upright body portion including a first inwardly extending portion terminating at a first inwardly facing surface, a first engagement surface of the first inwardly extending portion resting on a ridge of the alveolar arch of the patient, and (iii) a second upright body portion positioned at a second end of the horizontal body portion such that the second end of the horizontal body portion terminates at the second upright body portion, the second upright body portion including a second inwardly extending portion terminating at a second inwardly facing surface, a second engagement surface of the second inwardly extending portion resting on the ridge of the alveolar arch of the patient, the second inwardly extending portion extending toward the first inwardly extending portion such that the first inwardly facing surface and the second inwardly facing surface face each other, with a gap being defined between the first inwardly facing surface and the second inwardly facing surface; and (b) securing the first guide member relative to the alveolar arch of the patient, wherein the first upright body portion of the secured first guide member extends over a first occlusal region of the alveolar arch of the patient, wherein the second upright body portion of the secured first guide member extends over a second occlusal region of the alveolar arch of the patient, wherein the horizontal body portion of the secured first guide member is entirely positioned at a buccal region of the front-facing structure of the alveolar arch of the patient such that no region of the horizontal body is positioned at a palatal or lingual region of the alveolar arch of the patient.

2. The method of claim 1, the first upright body portion defining a first slot, the second upright body portion defining a second slot.

3. The method of claim 1, the horizontal body portion defining a plurality of openings extending from the second surface to the third surface.

4. The method of claim 1, the first engagement surface closely mating with a first bone structure of the ridge of the alveolar arch of the patient, the second engagement surface closely mating with a second bone structure of the ridge of the alveolar arch of the patient.

5. The method of claim 1, further comprising coupling the first guide member with a strut assembly, the strut assembly comprising:

(i) a horizontal body portion, the horizontal body portion of the strut assembly having an arcuate configuration generally corresponding to the arcuate configuration of the first guide member, (ii) a set of strut members, the act of coupling the first guide member with the strut assembly comprising engaging the strut members with the horizontal body portion of the first guide member, and (iii) a set of three-dimensional representations of teeth, the set of strut members positioning the teeth at a predetermined distance from the first surface of the first guide member.

6. The method of claim 5, the horizontal body portion of the strut assembly defining a pair of tabs at each end of the arcuate configuration, the first guide member defining a pair of slots, the act of coupling the first guide member with the strut assembly comprising inserting the pair of tabs into the pair of slots.

7. The method of claim 6, the pair of slots being defined by the first upright body portion and the second upright body portion.

8. The method of claim 5, the strut assembly further including one or more studs projecting from the horizontal body portion of the strut assembly opposite to the teeth, the one or more studs engaging corresponding regions of the ridge of the alveolar arch of the patient.

9. The method of claim 1, further comprising coupling the first guide member with a second guide member, the second guide member comprising:

(i) a horizontal body portion, the horizontal body portion of the second guide member having an arcuate configuration generally corresponding to the arcuate configuration of the first guide member, (ii) a set of flange members, the act of coupling the first guide member with the second guide member comprising engaging the set of flange members with the horizontal body portion of the first guide member, and (iii) a set of guide passageways.

10. The method of claim 9, the horizontal body portion of the second guide member having a horizontal surface, the act of coupling the first guide member with the second guide member comprising engaging the horizontal surface of the second guide member with the first surface of the horizontal body portion of the first guide member.

11. The method of claim 9, the horizontal body portion of the first guide member including a first set of openings, the flange members including second set of openings, the second set of openings aligning with the first set of openings, the method further comprising inserting fasteners through the first set of openings and the second set of openings are configured to receive fasteners while the second set of openings is aligned with the first set of openings.

12. The method of claim 9, the horizontal body portion of the second guide member defining a pair of tabs, one tab of the pair of tabs being positioned at each end of the arcuate configuration, the first guide member defining a pair of slots, the act of coupling the first guide member with the second guide member comprising inserting the pair of tabs into the pair of slots.

13. The method of claim 1, further comprising coupling the first guide member with a second guide member, the second guide member comprising:

(i) a horizontal body portion, the horizontal body portion of the second guide member having an arcuate configuration generally corresponding to the arcuate configuration of the first guide member, (ii) a set of flange members, the act of coupling the first guide member with the second guide member comprising engaging the set of flange members with the horizontal body portion of the first guide member, and (iii) a guide opening, the guide opening having an arcuate configuration extending along a portion of the horizontal body portion of the second guide member.

14. The method of claim 13, the horizontal body portion of the second guide member having a horizontal surface, the act of coupling the first guide member with the second guide member comprising engaging the horizontal surface of the second guide member with the first surface of the horizontal body portion of the first guide member, each flange member of the set of flange members having a rear surface engaging the second surface of the horizontal body portion of the first guide member.

15. The method of claim 13, the horizontal body portion of the second guide member defining a pair of tabs at each end of the arcuate configuration, the first guide member defining a pair of slots, the pair of slots being defined by the first upright body portion and the second upright body portion, the act of coupling the first guide member with the second guide member comprising inserting the pair of tabs into the pair of slots.

16. The method of claim 13, the horizontal body portion of the second guide member comprising a flat upper surface and a recessed surface extending from the flat upper surface to the guide opening, the recessed surface having a concave contour.

17. The method of claim 13, the second guide member further comprising a plurality of guide notches positioned along the guide opening.

18. The method of claim 13, the second guide member further comprising a plurality of marker features positioned along the guide opening.

19. A method comprising:
(a) coupling a first guide member with a strut assembly to form a combination, the first guide member comprising:
   (A) a horizontal body portion, the horizontal body portion having an arcuate configuration, the horizontal body portion including:
      (1) a first surface,
      (2) a second surface,
      (3) a third surface, and
      (4) a fourth surface opposite the first surface,
      the second surface and the third surface each extending between the first surface and the fourth surface,
   (B) a first upright body portion positioned at one end of the horizontal body portion, the first upright body portion including a first inwardly extending portion, and
   (C) a second upright body portion positioned at another end of the horizontal body portion, the second upright body portion including a second inwardly extending portion, and
the strut assembly comprising:
   (A) a horizontal body portion, the horizontal body portion of the strut assembly having an arcuate configuration generally corresponding to the arcuate configuration of the first guide member,
   (B) a set of strut members engaged with the horizontal body portion of the first guide member, the set of strut members including shelf portions, the shelf portions engaging the first surface and the second surface of the first guide member, and
   (C) a set of three-dimensional representations of teeth, the set of strut members positioning the teeth at a predetermined distance from the first surface of the first guide member; and
(b) securing the combination relative to an alveolar arch of a patient, such that:
   (i) the second surface of the horizontal body portion of the first guide member faces away from a front-facing structure of the alveolar arch of the patient,
   (ii) the third surface mates with the front-facing structure of the alveolar arch of the patient,
   (iii) a first engagement surface of the first inwardly extending portion rests on a first occlusal region of a ridge of the alveolar arch of the patient,
   (iv) a second engagement surface of the second inwardly extending portion rests on a second occlusal region of the ridge of the alveolar arch of the patient, and
   (v) the horizontal body portion of the first guide member is entirely positioned at a buccal region of the alveolar arch of the patient.

20. A method comprising:
(a) coupling a first guide member with a second guide member to form a combination, the first guide member comprising:
   (A) a horizontal body portion, the horizontal body portion having an arcuate configuration, the horizontal body portion including:
      (1) a first surface,
      (2) a second surface,
      (3) a third surface, and
      (4) a fourth surface opposite the first surface,
      the second surface and the third surface each extending between the first surface and the fourth surface,
   (B) a first upright body portion positioned at one end of the horizontal body portion, the first upright body portion including a first inwardly extending portion, and
   (C) a second upright body portion positioned at another end of the horizontal body portion, the second upright body portion including a second inwardly extending portion, and
the second guide member comprising:
   (A) a horizontal body portion, the horizontal body portion of the second guide member having an arcuate configuration generally corresponding to the arcuate configuration of the first guide member,
   (B) a set of flange members engaged with the horizontal body portion of the first guide member, each flange member of the set of flange members having a rear surface engaging the front surface of the horizontal body portion of the first guide member, and
   (C) a set of guide passageways; and
(b) securing the combination relative to an alveolar arch of a patient, such that:
   (i) the second surface of the horizontal body portion of the first guide member faces away from a front-facing structure of the alveolar arch of the patient,
   (ii) the third surface mates with the front-facing structure of the alveolar arch of the patient,
   (iii) a first engagement surface of the first inwardly extending portion rests on a first occlusal region of a ridge of the alveolar arch of the patient,
   (iv) a second engagement surface of the second inwardly extending portion rests on a second occlusal region of the ridge of the alveolar arch of the patient, and
   (v) the entire first guide member is entirely positioned at a buccal region of the front-facing structure of the alveolar arch of the patient, the first occlusal region of the ridge of the alveolar arch of the patient, and the second occlusal region of the ridge of the alveolar arch of the patient, such that no portion of the first guide member is positioned at a palatal or lingual region of the alveolar arch of the patient.

\* \* \* \* \*